(12) United States Patent  
Buchanan

(10) Patent No.: US 6,696,018 B2  
(45) Date of Patent: Feb. 24, 2004

(54) SYSTEM AND METHOD FOR STERILIZATION OF BIOLOGICAL CONNECTIONS

(75) Inventor: Brad Buchanan, Ross, CA (US)

(73) Assignee: Electron Process Company, LLC, Larkspur, CA (US)

( * ) Notice: Subject to any disclaimer, the term of this patent is extended or adjusted under 35 U.S.C. 154(b) by 152 days.

(21) Appl. No.: 09/993,367

(22) Filed: Nov. 14, 2001

(65) Prior Publication Data

US 2003/0091468 A1 May 15, 2003

(51) Int. Cl.$^7$ .................................................. A61L 2/00
(52) U.S. Cl. ..................... 422/22; 250/435; 250/455.11; 250/492.1; 250/492.3; 422/1; 422/23; 422/186.05
(58) Field of Search ................................ 422/1, 22, 23, 422/186.05; 250/455.11, 492.3, 492.1, 435

(56) References Cited

U.S. PATENT DOCUMENTS

| | | |
|---|---|---|
| 4,511,359 A | 4/1985 | Vaillancourt |
| 4,631,444 A * | 12/1986 | Cheever ...................... 313/420 |
| 5,141,592 A | 8/1992 | Shaposka et al. |
| 5,194,742 A * | 3/1993 | Avnery et al. ........... 250/492.3 |
| 5,209,800 A | 5/1993 | Spencer et al. |
| 5,256,229 A | 10/1993 | Spencer |
| 5,409,841 A | 4/1995 | Chow |
| 5,561,298 A | 10/1996 | Cirlin et al. |
| 5,612,588 A | 3/1997 | Wakalopulos |
| 5,656,491 A | 8/1997 | Cassani et al. |
| 5,744,811 A | 4/1998 | Schonberg et al. |
| 5,855,731 A | 1/1999 | Spencer |
| 5,932,132 A | 8/1999 | Plemons |
| 6,085,602 A | 7/2000 | Schorn et al. |
| 6,140,657 A | 10/2000 | Wakalopulos et al. |

OTHER PUBLICATIONS

Brochure, Sterilink Technologies, LLC, Nov. 1999, describing an early prototype of an apparatus for providing sterile connections between biological liquid systems.
Three (3) perspective drawings of inner structure of the early prototype.

* cited by examiner

*Primary Examiner*—Krisanne Thornton
(74) *Attorney, Agent, or Firm*—Knobbe, Martens, Olson & Bear, LLP

(57) ABSTRACT

A sterilization system seals a first end portion of a first tube and a second end portion of a second tube under sterile conditions. The sterilization system includes a sterilization chamber and an electron gun which generates a distribution of electrons in the sterilization chamber. The sterilization system further includes a spindle and a holder which places and rotates a connector in the distribution of electrons. The sterilization system further includes first and second tube holders each having curved walls movably coupled to the sterilization chamber to move between a first position where the respective end portion is separated from the connector and a second position where the respective end portion is coupled to the connector. Each curved wall has a shape such that x rays generated within the sterilization chamber undergo at least three interactions with the curved walls before propagating outside the tube holders.

48 Claims, 23 Drawing Sheets

SYSTEM AND METHOD FOR STERILIZATION OF BIOLOGICAL CONNECTIONS

BACKGROUND OF THE INVENTION

1. Field of the Invention

The present invention relates to sterilization systems and methods, and more particularly to sterilization systems and methods used in conjunction with biological systems such as bioreactors.

2. Description of the Related Art

The manufacture of various chemicals, such as enzymes, pharmaceuticals, antibodies, and vaccines, often require the growth of microorganisms or cells in a controlled fermentation chamber, typically called a bioreactor. Operation of such a bioreactor includes connecting and disconnecting various modules from the bioreactor, such as media or sampling vessels. To maintain the bioreactor and modules in aseptic condition, i.e., containing only desired organisms, as well as to avoid releasing potentially harmful organisms to the environment, these connections and disconnections are advantageously made under sterile conditions.

SUMMARY OF THE INVENTION

One aspect of embodiments of the present invention provides a sterilization system that seals a first end portion of a first tube and a second end portion of a second tube under sterile conditions. The sterilization system comprises a sterilization chamber and an electron gun coupled to the sterilization chamber. The electron gun generates a distribution of electrons in the sterilization chamber. The electrons generate x rays upon impinging surfaces within the sterilization chamber. The sterilization system further comprises a spindle having at least a portion in the sterilization chamber. The spindle is rotatably and linearly positionable with respect to the distribution of electrons. The sterilization system further comprises a holder coupled to the spindle. The holder releasably positioning the spindle places the connector in the distribution of electrons and whereby rotating the spindle rotates the connector within the distribution of electrons. The sterilization system further comprises first and second tube holders which receive the first and second tubes respectively. Each tube holder has curved walls movably coupled to the sterilization chamber to move between a first position where the respective end portion is separated from the connector and a second position where the respective end portion is coupled to the connector. Each curved wall has a shape such that the x rays generated within the sterilization chamber undergo at least three interactions with the curved walls before propagating outside the tube holders.

Another aspect of embodiments of the present invention provides a method of sealing together under sterile conditions a first end portion of a first tube and a second end portion of a second tube. Sealing the first and second tubes prevents transport of microorganisms across the respective end portions. The method comprises receiving a connector in a sterilization chamber. The method further comprises receiving the first tube in a first tube holder. The first tube holder has curved walls movably coupled to the sterilization chamber. The method further comprises receiving the second tube in a second tube holder. The second tube holder has curved walls movably coupled to the sterilization chamber. The method further comprises receiving the first end portion and the second end portion in the sterilization chamber. The method further comprises irradiating the connector, the first end portion, and the second end portion with a distribution of electrons. The method further comprises coupling the first end portion to the connector. The method further comprises coupling the second end portion to the connector, thereby providing fluid coupling between the first and second tubes and preventing transport of microorganisms between an interior of the tubes and an exterior of the tubes.

Another aspect of embodiments of the present invention provides a method of sealing together under sterile conditions a first end portion of a first tube and a second end portion of a second tube. The first end portion is initially plugged by a first plug and the second end portion is initially plugged by a second plug. Plugging the first and second end portions prevents transport of microorganisms across the respective end portion. The method comprises receiving a connector in a sterilization chamber of a sterilization system. The method further comprises receiving the first end portion and the second end portion in the sterilization chamber. The method further comprises unplugging the first end portion by removing the first plug from the first end portion. The method further comprises unplugging the second end portion by removing the second plug from the second end portion. The method further comprises irradiating the connector, the first end portion, and the second end portion with a distribution of electrons. The method further comprises coupling the first end portion to the connector. The method further comprises coupling the second end portion to the connector, thereby providing fluid coupling between the first and second tubes and preventing transport of microorganisms between an interior of the tubes and an exterior of the tubes Another aspect of embodiments of the present invention provides a method of sealing closed under sterile conditions a first end portion of a first tube. The first end portion is initially sealed together via a connector with a second end portion of a second tube to provide fluid coupling between the first and second tubes. The method comprises receiving the connector, the first end portion, and the second end portion in a sterilization chamber. The method further comprises receiving a first plug in the sterilization chamber. The method further comprises detaching the first end portion from the connector. The method further comprises irradiating the first plug with a distribution of electrons. The method further comprises coupling the first end portion to the first plug, thereby preventing transport of microorganisms between an interior of the first tube and an exterior of the first tube.

Another aspect of embodiments of the present invention provides a method of sealing closed under sterile conditions an end portion of a tube. The method comprises receiving the tube in a tube holder having curved walls movably coupled to a sterilization chamber. The end portion extends into the sterilization chamber. The method further comprises receiving a plug in the sterilization chamber. The method further comprises irradiating the plug with a distribution of electrons. The method further comprises coupling the end portion to the plug by moving the curved walls of the tube holder between a first position where the end portion is separated from the plug and a second position where the end portion is coupled to the plug, thereby preventing transport of microorganisms between an interior of the tube and an exterior of the tube.

Another aspect of embodiments of the present invention provides a connector for coupling a first tube to a second tube. The first tube has a first tube wall with a first inner surface and a first outer surface. The first tube wall defines a first interior region and a first exterior region of the first tube. The second tube has a second tube wall with a second inner surface and a second outer surface. The second tube wall defines a second interior region and a second exterior region of the second tube. The connector comprises a body and a generally cylindrical first bore extending from a center portion of the body to a first distal portion of the body and having a first axis and a flared first inner bore surface. The connector further comprises a first annular barb fitting around the first distal portion of the body. The connector further comprises a generally cylindrical second bore extending from the center portion of the body to a second distal portion of the body and having a second axis and a flared second inner bore surface. The first bore and second bore define a conduit through which fluid can flow. The connector further comprises a second annular barb fitting around the second distal portion of the body. The connector further comprises a first retaining collar around the body. The first retaining collar has a flared first inner collar surface. The first retaining collar provides a first positive connection with the first tube. The first positive connection prevents transport of microorganisms between the first interior region and the first exterior region of the first tube. The connector further comprises a second retaining collar around the body. The second retaining collar has a flared second inner collar surface. The second retaining collar provides a second positive connection with the second tube. The second positive connection prevents transport of microorganisms between the second interior region and the second exterior region of the second tube.

Another aspect of embodiments of the present invention provides a plug for sealing a tube having a tube wall with an inner surface and an outer surface. The tube wall defines an interior region and an exterior region of the tube. The plug comprises a plug body and a center portion of the plug body adapted to be held by a holder and supported by the arcuate surface of a connector. The connector comprises a connector body and a generally cylindrical first bore extending from a center portion of the connector body to a first distal portion of the connector body and having a first axis and a flared first inner bore surface. The connector further comprises a first annular barb fitting around the first distal portion of the connector body. The connector further comprises a generally cylindrical second bore extending from the center portion of the connector body to a second distal portion of the connector body and having a second axis and a flared second inner bore surface. The first bore and second bore define a conduit through which fluid can flow. The connector further comprises a second annular barb fitting around the second distal portion of the connector body. The connector further comprises a first retaining collar around the connector body. The first retaining collar has a flared first inner collar surface. The connector further comprises a second retaining collar around the connector body. The second retaining collar has a flared second inner collar surface. The plug further comprises a generally cylindrical stopper portion extending from the center portion of the plug body to a distal portion of the plug body. The plug further comprises a third annular barb fitting around the distal portion of the plug body and a third retaining collar around the plug body. The third retaining collar has a flared inner collar surface. The third retaining collar provides a positive connection with the tube. The positive connection prevents transport of microorganisms between the interior region and the exterior region of the tube.

DETAILED DESCRIPTION OF THE PREFERRED EMBODIMENT

Figure 1:
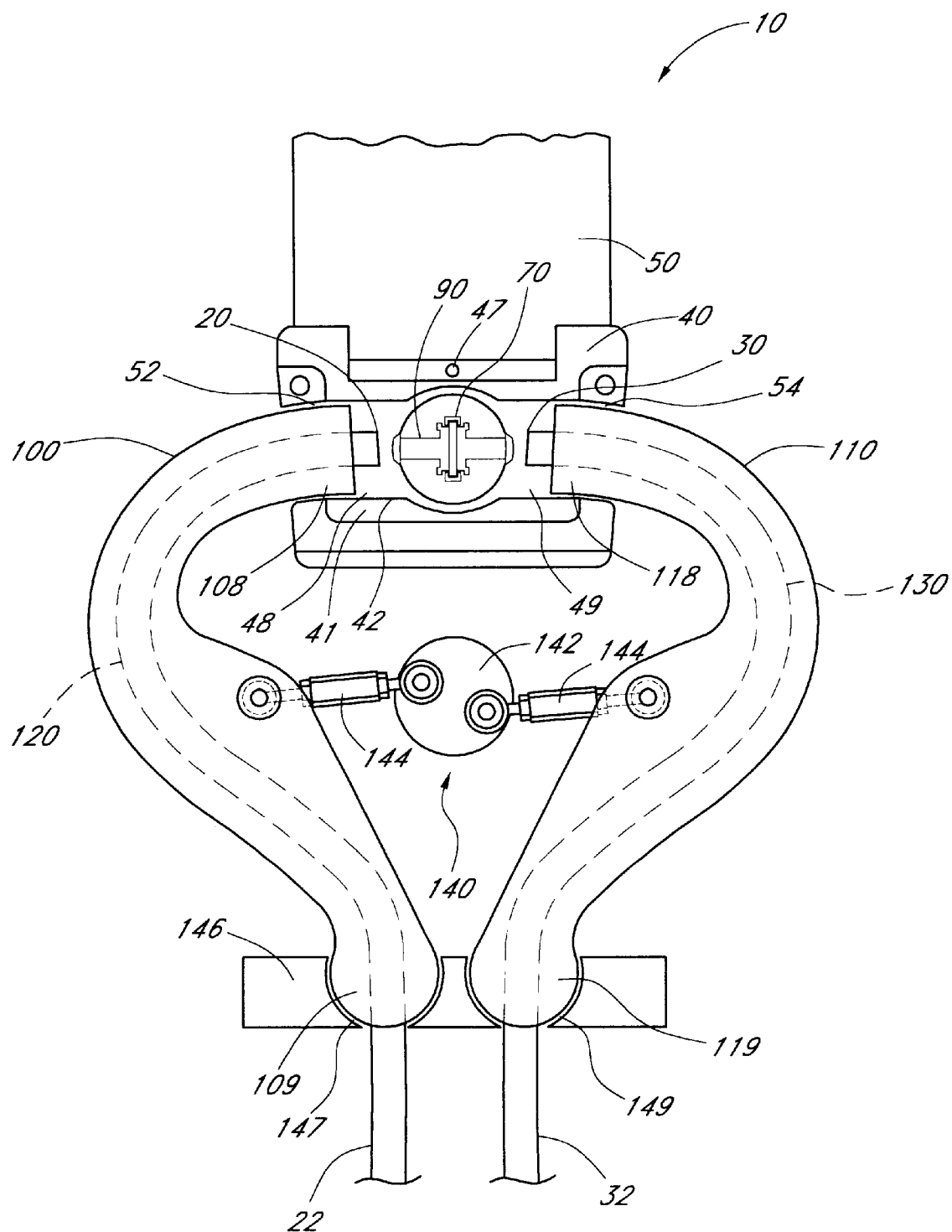
FIG. 1 schematically illustrates a top view of a sterilization system in accordance with an embodiment of the present invention.
Figure 2:
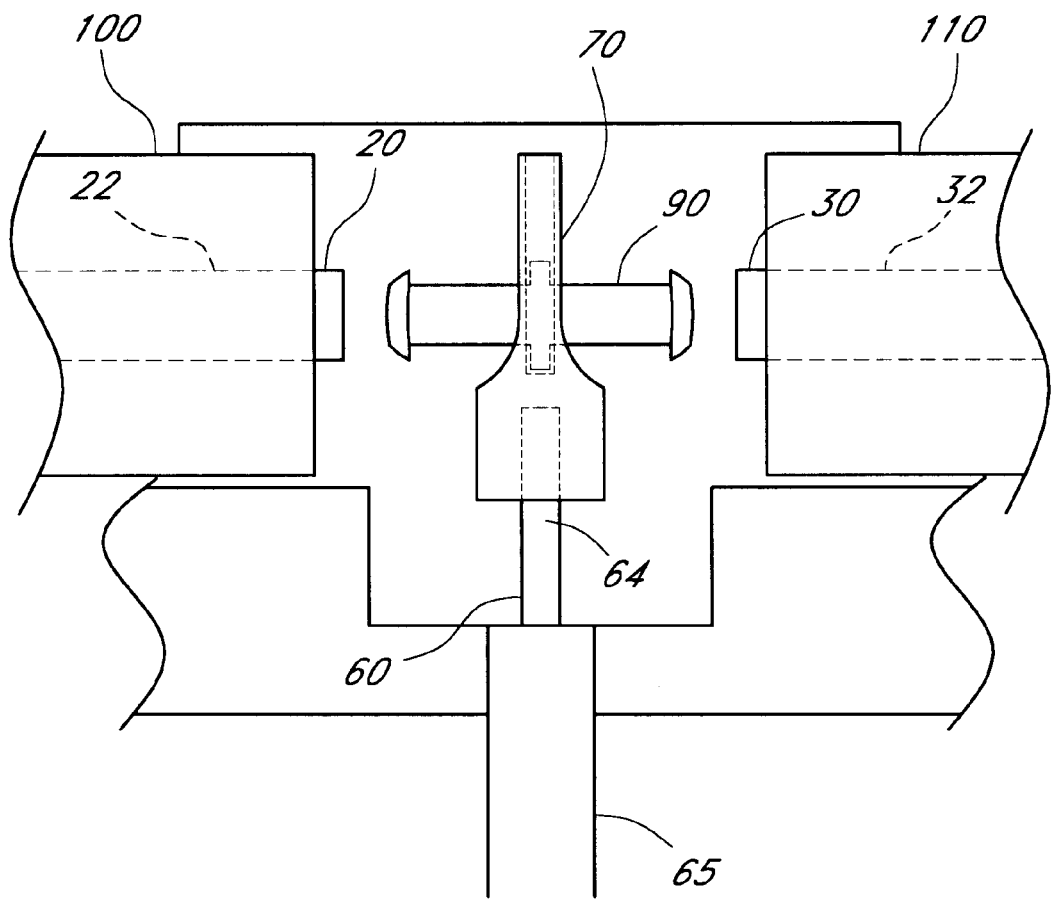
FIG. 2 schematically illustrates a cross-section of a sterilization chamber in accordance with an embodiment of the present invention.

As schematically illustrated in FIGS. 1 and 2, one embodiment of the present invention comprises a sterilization system 10 that seals a first end portion 20 of a first tube 22 and a second end portion 30 of a second tube 32 under sterile conditions. The sterilization system 10 comprises a sterilization chamber 40 and an electron gun 50. The electron gun 50 is coupled to the sterilization chamber 40. The electron gun 50 generates a distribution of electrons in the sterilization chamber 40. The electrons generate x rays upon impinging surfaces within the sterilization chamber 40. The sterilization system 10 further comprises a spindle 60 having at least a portion in the sterilization chamber 40. The spindle 60 is rotatably and linearly positionable with respect to the distribution of electrons. The sterilization system 10 further comprises a holder 70 coupled to the spindle 60, the holder 70 releasably receiving a connector 90. Linearly positioning the spindle 60 places the connector 90 in the distribution of electrons, and rotating the spindle 60 rotates the connector 90 within the distribution of electrons.

The sterilization system 10 further comprises first and second tube holders 100, 110 which receive the first and second tubes 22, 32 respectively. Each tube holder 100, 110 has curved walls 120, 130 which are movably coupled to the sterilization chamber 40 to move between a first position where the respective end portion 20, 30 is separated from the connector 90 and a second position where the respective end portion 20, 30 is coupled to the connector 90. Each curved wall 120 has a shape such that the x rays generated within the sterilization chamber 40 undergo at least three interactions with the curved walls 120, 130 before propagating outside the tube holders 100, 110.

Certain embodiments of the sterilization system 10 are adapted for use with bioreactor systems which require connection and disconnection of various modules from the bioreactor system under sterile conditions. Examples of such modules include, but are not limited to, media vessels and sampling vessels. These modules are typically connected to the rest of the bioreactor system by tubing which provides sterile, fluid connection between the module and the rest of the bioreactor system. Such tubing allows transfer of liquid material between the module and the bioreactor system while avoiding contamination of the inside of the bioreactor system from microorganisms outside the bioreactor system. In addition, the tubing prevents microorganisms inside the bioreactor system from escaping to outside the bioreactor system. Examples of tubing materials compatible with embodiments of the present invention include, but are not limited to, polyethylene, polyproplyene, polyamide, polyurethane, polytetrafluoroethylene such as Teflon® available from E. I. du Pont Nemours and Company of Wilmington, Del., silicone, polyvinyldene fluoride, and vinyl. Embodiments of the present invention provide the ability to make connections and disconnections between the modules and the rest of the bioreactor system by sealing the first end portion 20 of a first tube 22 and a second end portion 30 of a second tube 32 under sterile conditions.

In certain embodiments, as schematically illustrated in FIG. 1, the sterilization chamber 40 comprises chamber walls 41 with metallic inside surfaces 42. Metallic inside surfaces 42 compatible with embodiments of the present invention include, but are not limited to, stainless steel and hard coat anodized aluminum. As is described more fully below, electrons from the electron gun 50 impinging the metallic inside surfaces 42 of the sterilization chamber 40 interact with the metallic inside surfaces 42 and generate x rays. In addition, the metallic inside surfaces 42 prevent x rays from propagating through the chamber walls 41 to outside the sterilization chamber 40.

Figure 3:
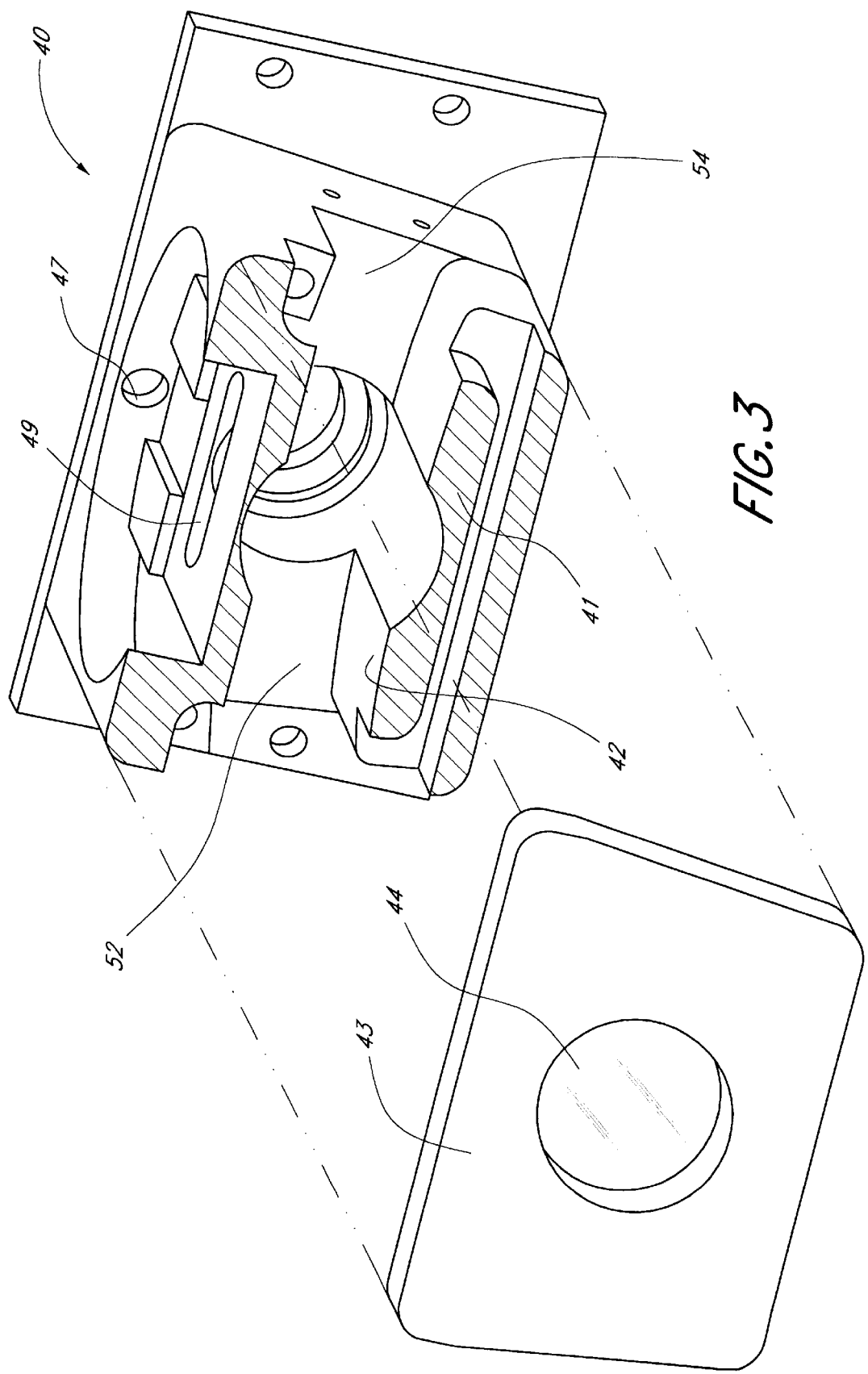
FIG. 3 schematically illustrates a perspective view of a sterilization chamber and cover in accordance with an embodiment of the present invention.

The sterilization chamber 40 of certain embodiments, as schematically illustrated in FIG. 3, comprises a cover 43 with a leaded glass window 44. Opening the cover 43 provides access to the interior of the sterilization chamber 40 at the start and end of the sealing procedure, as described more fully below. The leaded glass window 44 allows a user to inspect the inside of the sterilization chamber 40 during the sealing procedure while the cover 43 is closed. As described more fully below, when closed, the cover 43 and leaded glass window 44 prevent x rays from propagating outside the sterilization chamber 40 during the sealing procedure. In certain embodiments, the cover 43 is removable from the sterilization chamber 40. In certain other embodiments, the cover 43 is hingedly coupled to the sterilization chamber 40 so that the cover 43 can be pivoted away from the sterilization chamber 40 to provide access to the interior of the sterilization chamber 40. The cover 43 of certain embodiments includes a cover interlock 45 which generates a signal indicative of whether the cover 43 is opened or closed.

Figure 4:
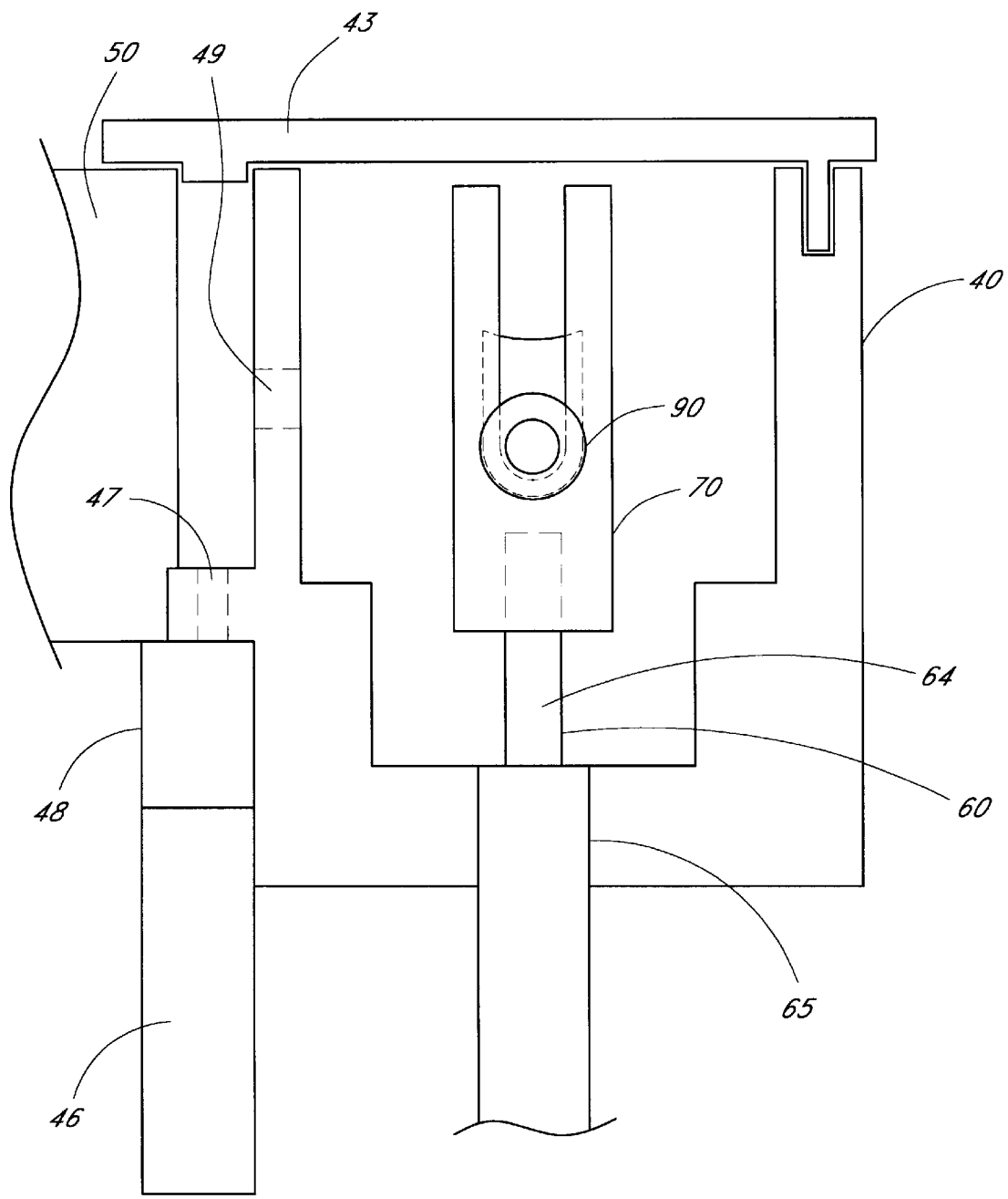
FIG. 4 schematically illustrates another cross-section of a sterilization chamber in accordance with an embodiment of the present invention.

In certain embodiments, as schematically illustrated in FIG. 3, the sterilization chamber 40 further comprises a gas hole 47 and an electron hole 49. As schematically illustrated in FIG. 4, in such embodiments the sterilization chamber 40 is coupled to a gas source 46 via the gas hole 47, the gas source 46 supplying a controlled quantity of gas to the sterilization chamber 40. The gas source 46 of certain embodiments includes a gas valve 48 which is responsive to electrical signals to open or close.

The gas hole 47 is in fluid communication with an interior of the sterilization chamber 40 via the electron hole 49. When the cover 43 is closed, the sterilization chamber 40 can be filled with gas flowing from the gas source 46 through the gas hole 47 and through the electron hole 49 as part of certain embodiments of the sealing procedure. In embodiments in which the electron gun 50 is activated while gas is flowed into the sterilization chamber 40, the gas is irradiated by the electron beam while the gas is in the region between the gas hole 47 and the electron hole 49. In this way, the level of any biological contamination in the gas is reduced before the gas enters the sterilization chamber 40.

Examples of gases compatible with embodiments of the present invention include, but are not limited to, helium and nitrogen. During certain embodiments of the sealing procedure, the gas atoms or molecules are ionized by the electrons from the electron gun 50, forming a plasma which can contribute to the sterile field in the sterilization chamber 40.

In certain embodiments, the electron gun 50 comprises at least one electron beam tube which generates a low energy electron beam. Examples of such electron guns 50 are described by Wakalopulos, et al., in U.S. Pat. Nos. 6,140,657 and 5,612,588, both of which are incorporated in their entirety by reference herein. In such embodiments, electrons are emitted from a cathode, and accelerated and focused by electrostatic and magnetic fields in a region of low vacuum pressure to form an electron beam with kinetic energy of less than approximately 100 keV. Typically, the electron beam tube has a thin window separating the region of low vacuum pressure within the electron gun from the sterilization chamber 40. The window is permeable to the electron beam, but impermeable to the atoms and molecules which comprises the gases in the sterilization chamber 40, so that the electron beam can enter the sterilization chamber 40 while maintaining the low vacuum pressure inside the electron gun 50.

Once inside the sterilization chamber 40, the incident electrons comprising the electron beam impinge on various surfaces of the sterilization chamber 40, holder 70, connector 90, and anything else in the sterilization chamber 40. Some of the incident electrons are reflected back from these surfaces, either elastically or inelastically. Some of the incident electrons excite other electrons from these surfaces, termed secondary electrons. The incident electrons, reflected electrons, and secondary electrons comprise a distribution of electrons in the sterilization chamber 40.

In certain embodiments, the spindle 60 of the sterilization chamber 40 comprises a rod 64 which is coupled to the rest of the sterilization chamber 40 so that the rod 64 can be rotated about its axis and linearly translated along its axis, such that the spindle 60 is rotatably and linearly positionable with respect to the distribution of electrons. Typically, the rod 64 is metallic, comprising stainless steel or hard coat anodized aluminum, but persons skilled in the art are able to select other materials in accordance with embodiments of the present invention.

As schematically illustrated in FIGS. 2 and 4, in certain embodiments, a first portion of the spindle 60 extends into the sterilization chamber 40, and a second portion of the spindle 60 extends out of the sterilization chamber 40 where it is coupled to one or more spindle actuators 65. Examples of spindle actuators 65 compatible with embodiments of the present invention include, but are not limited to, stepper motors and oil-over-air cylinders. To provide both the rotation and linear translation of the spindle 60, certain embodiments utilize a rotation spindle actuator and a linear spindle actuator. The rotation spindle actuator of certain embodiments comprises a rack-and-pinion configuration coupled to a linear motion actuator. In embodiments in which the rotation spindle actuator and linear spindle actuator are responsive to control signals, the spindle actuators 65 are used to selectively rotate and linearly translate the spindle 60 with respect to the distribution of electrons within the sterilization chamber 40. Persons skilled in the art are able to provide spindle actuators 65 in accordance with embodiments of the present invention.

Figure 5:
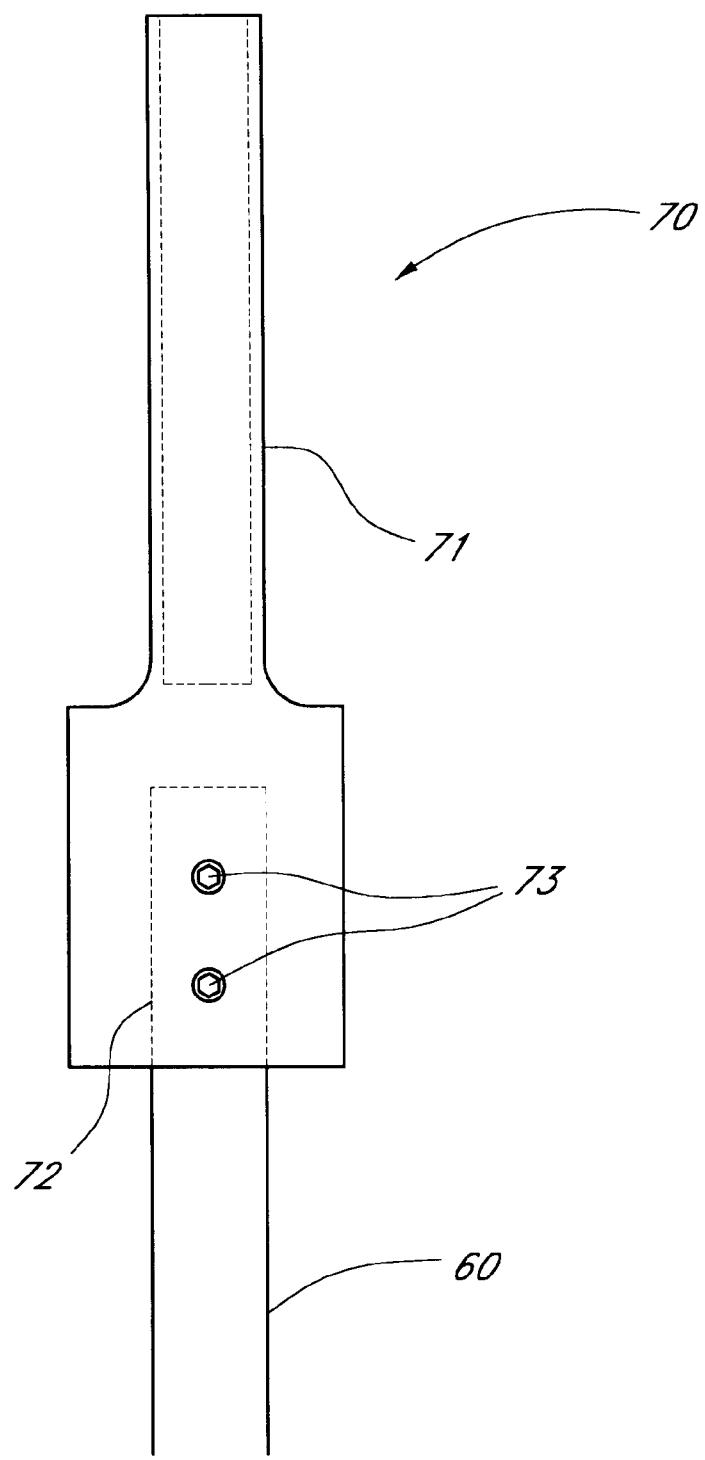
FIG. 5 schematically illustrates a side view of a holder in accordance with an embodiment of the present invention.

The holder 70 of certain embodiments is coupled to the spindle 60 whereby linearly positioning the spindle 60 translates the holder 70 with respect to the distribution of electrons and rotating the spindle 60 also rotates the holder 70. As is described more fully below, the holder 70 of certain embodiments is adapted to releasably receive a connector 90. As schematically illustrated in FIG. 5, the holder 70 comprises a slotted fork portion 71 into which the connector 90 fits. In certain embodiments, the holder 70 also comprises a generally cylindrical hole 72 in which the spindle 60 is held by set screws 73. Persons skilled in the art are able to select an appropriate coupling between the holder 70 and the spindle 60 in accordance with embodiments of the present invention.

As schematically illustrated in FIG. 1, the first tube holder 100 and the second tube holder 110 of certain embodiments have curved walls 120, 130, respectively, which are movably coupled to the sterilization chamber 40. The curved walls 120, 130 are adapted to receive the first tube 22 and the second tube 32, respectively, such that the first end portion 20 of the first tube 22 and the second end portion 30 of the second tube 32 are in the sterilization chamber 40. As used herein, the term "curved walls" refers to the general "S"-like shape of the walls 120, 130 which extends along a lateral direction from the chamber ends 108, 118 to the pivot ends 109, 119 the first and second tube holders 100, 110, respectively. Other curved shapes can also be used advantageously to suppress emission of x rays, as described herein. The cross-section of the walls 120, 130 perpendicular to this lateral direction can be circular, square, or other shapes compatible with embodiments of the present invention.

In certain embodiments, the curved walls 120, 130 comprise a metallic surface which can include, but are not limited to, stainless steel and hard coat anodized aluminum. Persons skilled in the art are able to provide metallic surfaces in accordance with embodiments of the present invention.

Figure 6:
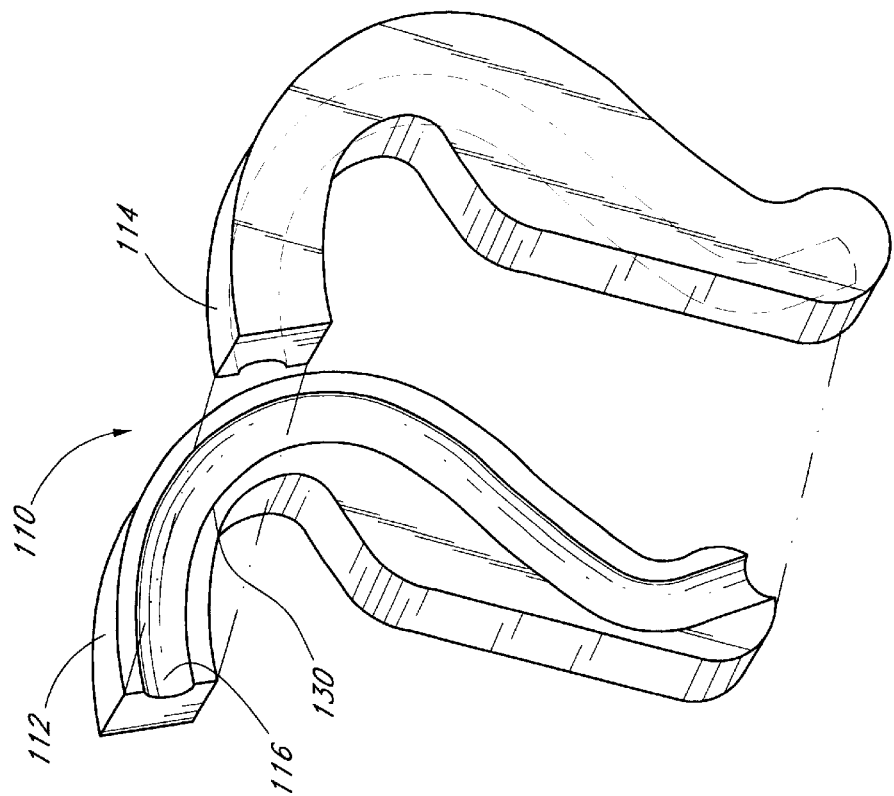
FIG. 6 schematically illustrates a perspective view of a first bottom portion, first top portion, second bottom portion, and second top portion of first and second tube holders in accordance with an embodiment of the present invention.
Figure 6:
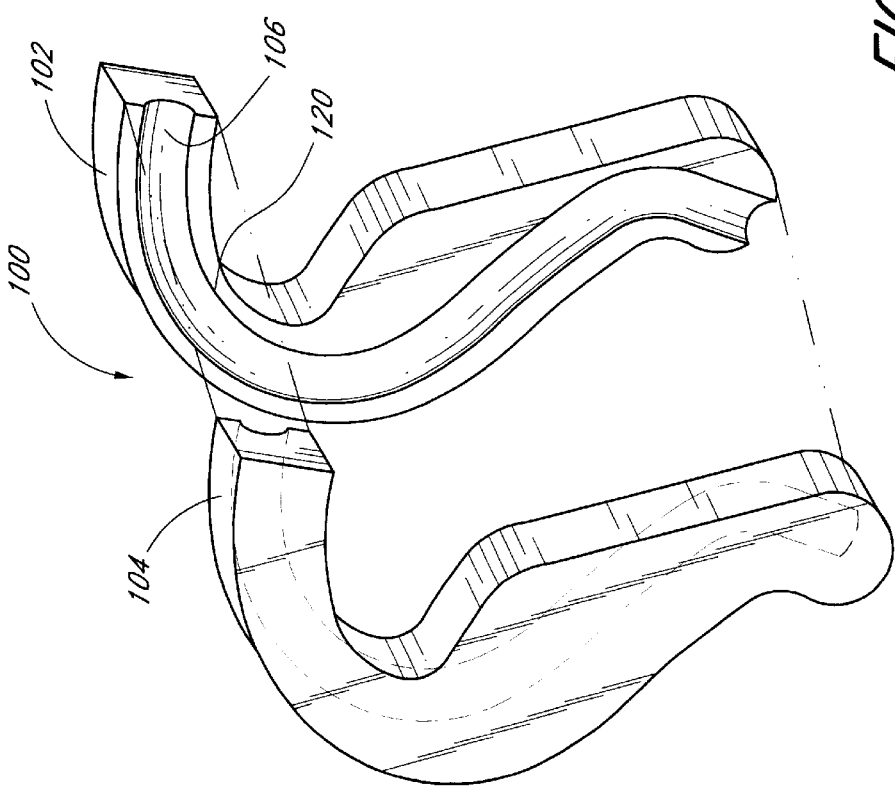

In the embodiment schematically illustrated in FIG. 6, the first tube holder 100 comprises a first bottom portion 102 and a first top portion 104 which fit together to form the first tube holder 100. When the first bottom portion 102 and first top portion 104 are fit together, the first curved wall 120 defines a first space 106 into which the first tube 22 is received. The first bottom portion 102 and first top portion 104 can be separated, and then replaced, to facilitate insertion and removal of the first tube 22 from the first tube holder 100. Similarly, the second tube holder 110 comprises a second bottom portion 112 and a second top portion 114 which fit together so that the second curved wall 130 defines a second space 116 into which the second tube 32 is received.

In certain embodiments, the first tube holder 100 has a first chamber end 108 which is movably coupled to the sterilization chamber to slide along a first channel 52 of the sterilization chamber 40. Similarly, the second tube holder 110 has a second chamber end 118 which is movably coupled to slide along a second channel 54 of the sterilization chamber 40. The first chamber end 108 and second chamber end 118 each provide a portion of the enclosure of the sterilization chamber 40, as in the embodiment schematically illustrated by FIGS. 1 and 3.

In certain embodiments, the first and second tube holders 100, 110 are coupled to a tube actuator 140 which moves the curved walls 120, 130 of the first and second tube holders 100, 110 between the first position and the second position. As schematically illustrated in FIG. 1, in certain embodiments, the tube actuator 140 comprises a rotatable wheel 142, arms 144, and a pivot support 146. The pivot support 146 includes a generally circular first recess 147 and a generally circular second recess 149. The arms 144 are rotatably coupled to the rotatable wheel 142 at positions away from the center of the wheel 142. The arms 144 are further rotatably coupled to the first and second tube holders 100, 110.

Figure 7A:
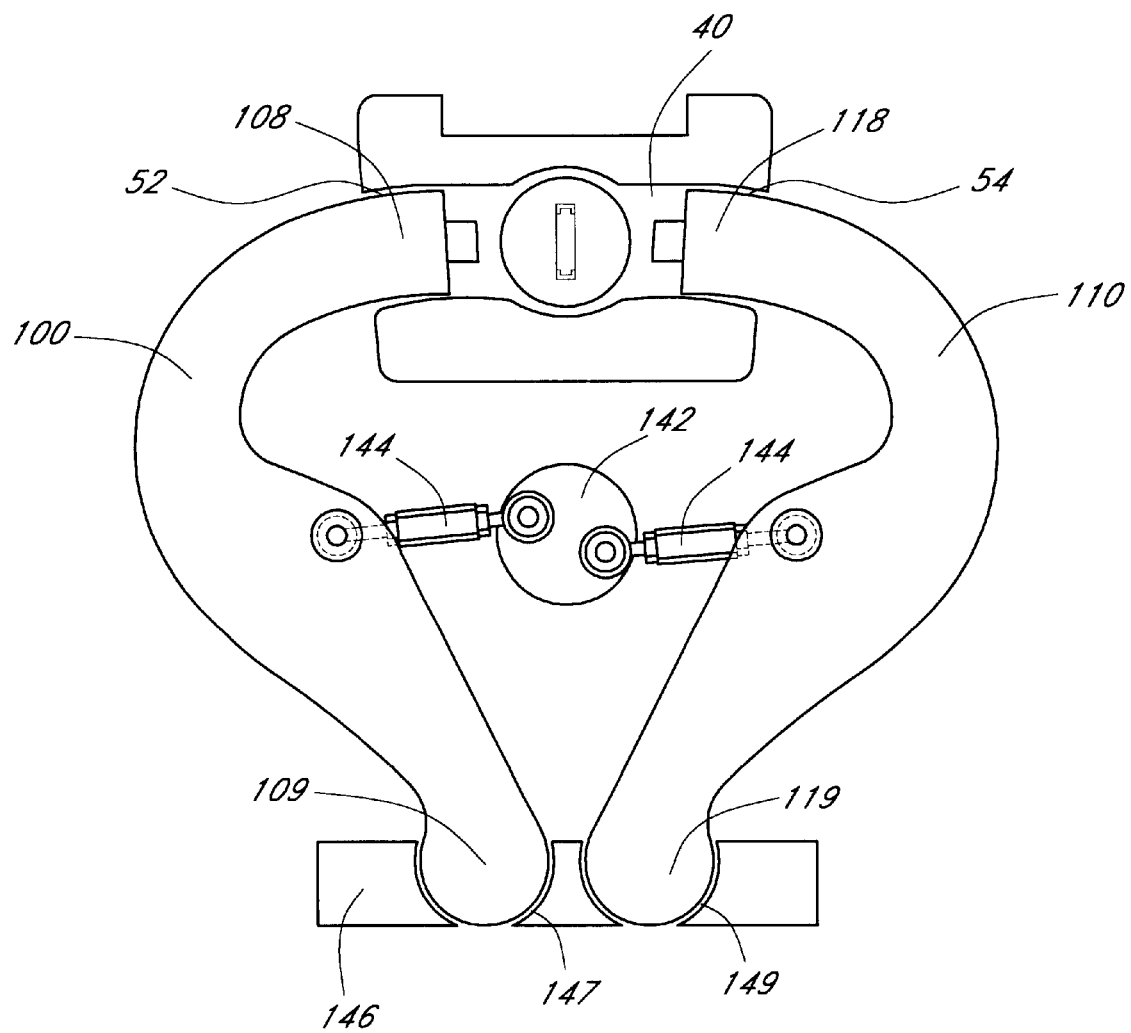
FIG. 7A schematically illustrates a sterilization system in the first position in accordance with embodiments of the present invention.
Figure 7B:
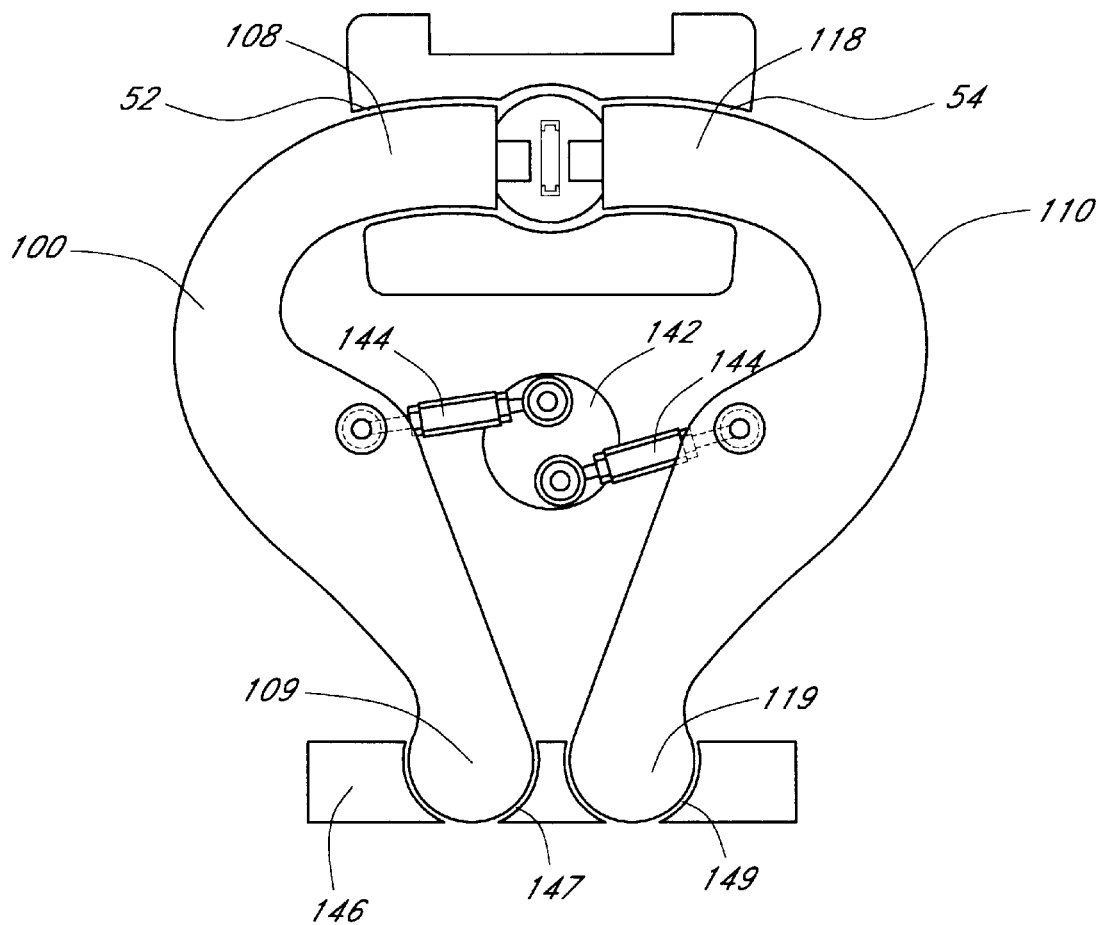
FIG. 7B schematically illustrates a sterilization system in the second position in accordance with embodiments of the present invention.

In the embodiment schematically illustrated in FIG. 1, the first tube holder 100 further comprises a first pivot end 109 which is held in place by the first recess 147 of the pivot support 146, such that the first tube holder 100 can be pivoted about the first pivot end 109 to move the first chamber end 108. Similarly, the second tube holder 110 further comprises a second pivot end 119 which is held in place by the second recess 149, such that the second tube holder 110 can be pivoted about the second pivot end 119 to move the second chamber end 118. In this way, rotation of the wheel 142 can be utilized to move the curved walls 120, 130 of the first and second tube holders 100, 110 between the first position and the second position. The first position, as schematically illustrated in FIG. 7A, has the first chamber end 108 and second chamber end 118 positioned away from the holder 70 and each other. The second position, as schematically illustrated in FIG. 7B, has the first chamber end 108 and second chamber end 118 positioned towards the holder 70 and each other. Persons skilled in the art are able to provide other configurations of tube holders 100, 110 having curved walls 120, 130 movably coupled to the sterilization chamber 40 in accordance with embodiments of the present invention.

Figure 8:
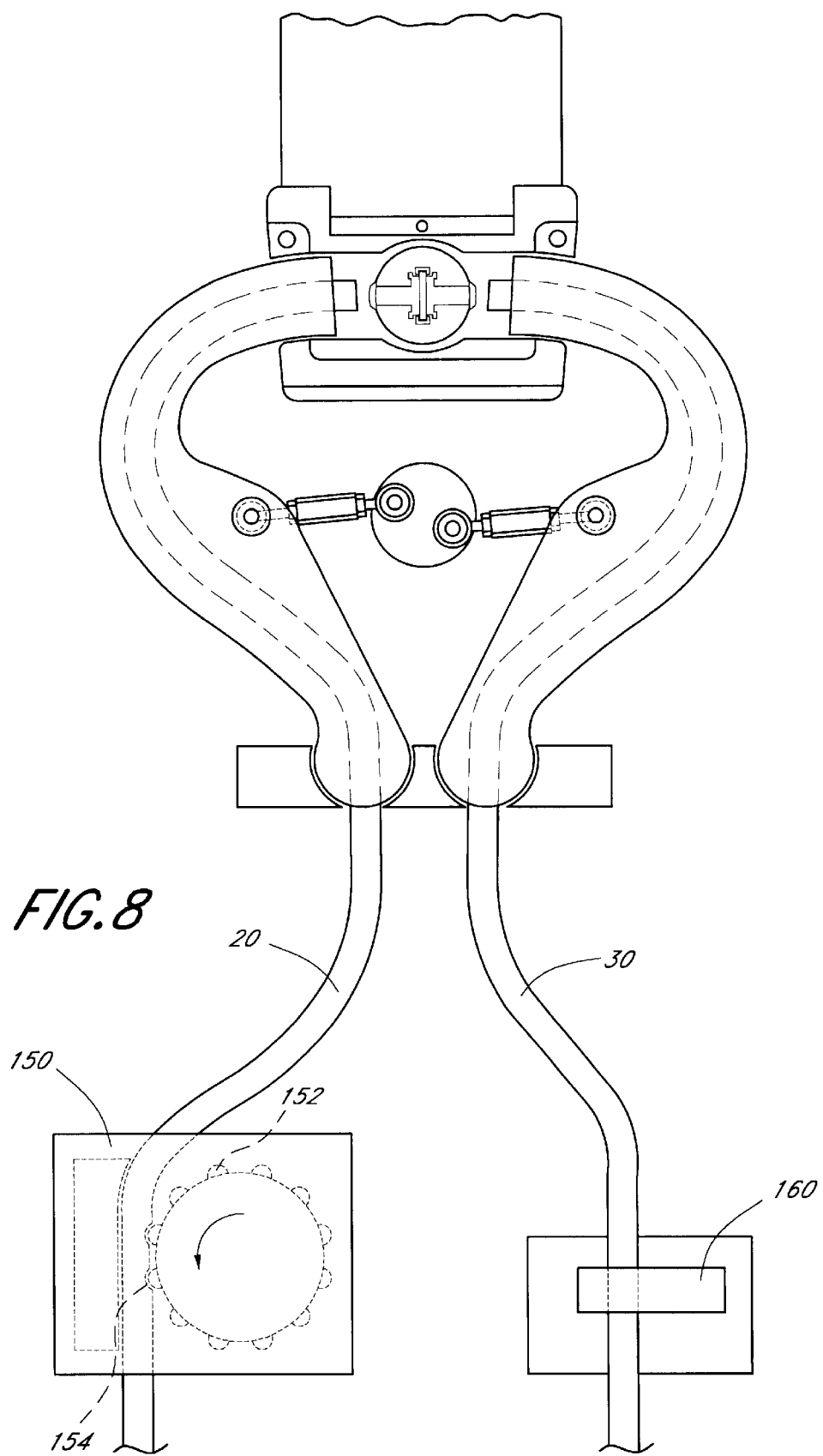
FIG. 8 schematically illustrates a top view of a sterilization system comprising a peristaltic pump and clamp in accordance with an embodiment of the present invention.

In certain embodiments, the sterilization system 10 further comprises a peristaltic pump 150 which is connectable to the first tube 20, as schematically illustrated in FIG. 8. In typical operation, the first tube 20 is placed in the peristaltic pump 150, and rollers 152 are placed in contact with the first tube 20 so as to form compressions 154 of the first tube 20. As the rollers 152 are rolled along a portion of the first tube 20, the compressions 154 also travel along the first tube 20. In this way, in embodiments in which the first tube 20 is sealed closed, the peristaltic pump 150 can reduce the pressure inside the first tube 20 as compared to the pressure outside the first tube 20.

In certain embodiments, the sterilization system 10 further comprises a tube clamp 160 which is connectable to the second tube 30, as schematically illustrated in FIG. 8. In typical operation, the second tube 30 is placed in the tube clamp 160, and the tube clamp 160 is then closed to compress and thereby temporarily seal the second tube 30. The operation of the tube clamp 160 is automated in certain embodiments using a clamp actuator 162 that is responsive to electrical signals. In embodiments in which the first tube 20 and second tube 30 are sealed together via a connector 90, using the peristaltic pump 150 and the tube clamp 160 can reduce the pressure inside both the first tube 20 and second tube 30.

Figure 9:
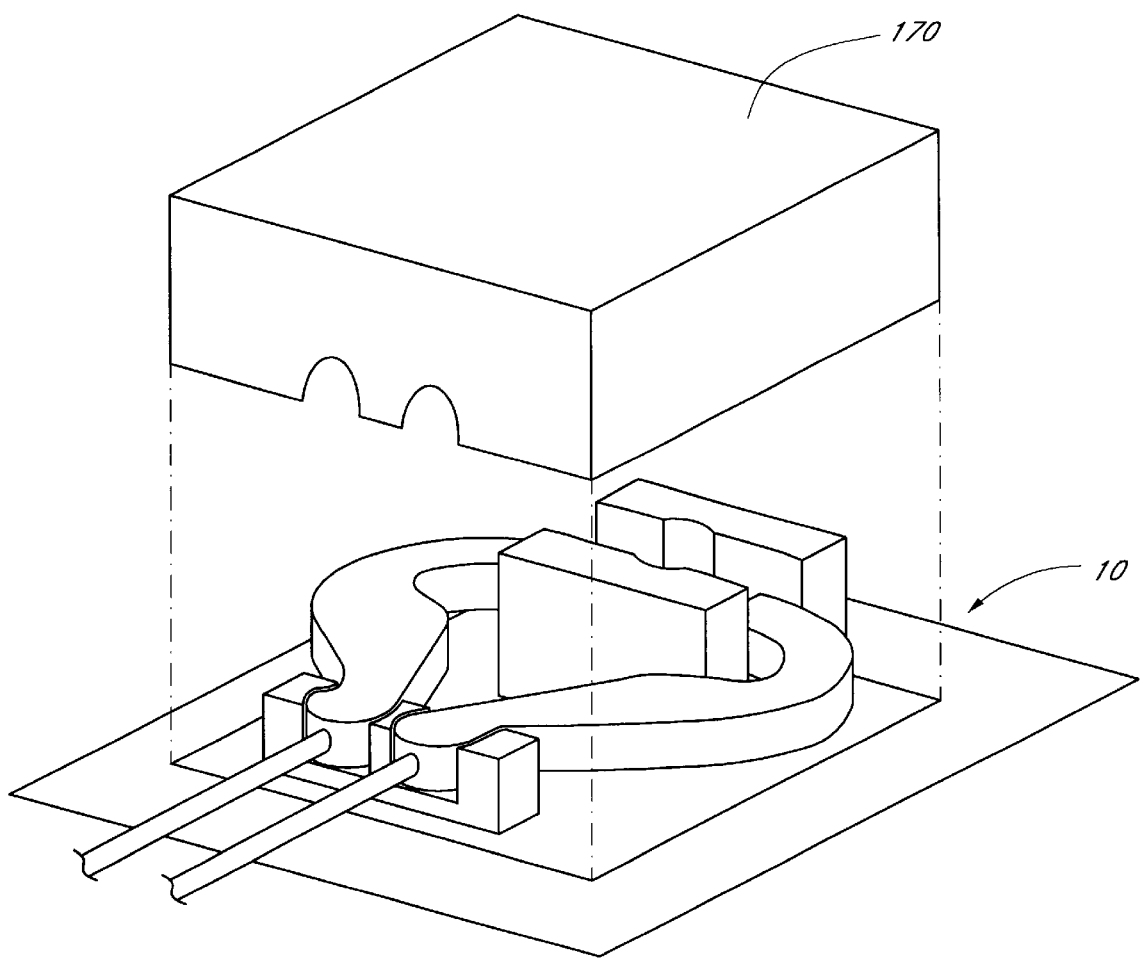
FIG. 9 schematically illustrates a perspective view of a sterilization system comprising a system cover in accordance with an embodiment of the present invention.

In certain embodiments, as schematically illustrated in FIG. 9, the sterilization system 10 further comprises a system cover 170 which can be placed over the other components of the sterilization system 10. Once the system cover 170 is in place, the possibility of injury to a user is reduced by preventing inappropriate access during operation of the sterilization system 10. In certain embodiments, the system cover 170 has a system cover interlock 172 which provides a signal indicative of whether the system cover 170 is opened or closed.

Figure 10:
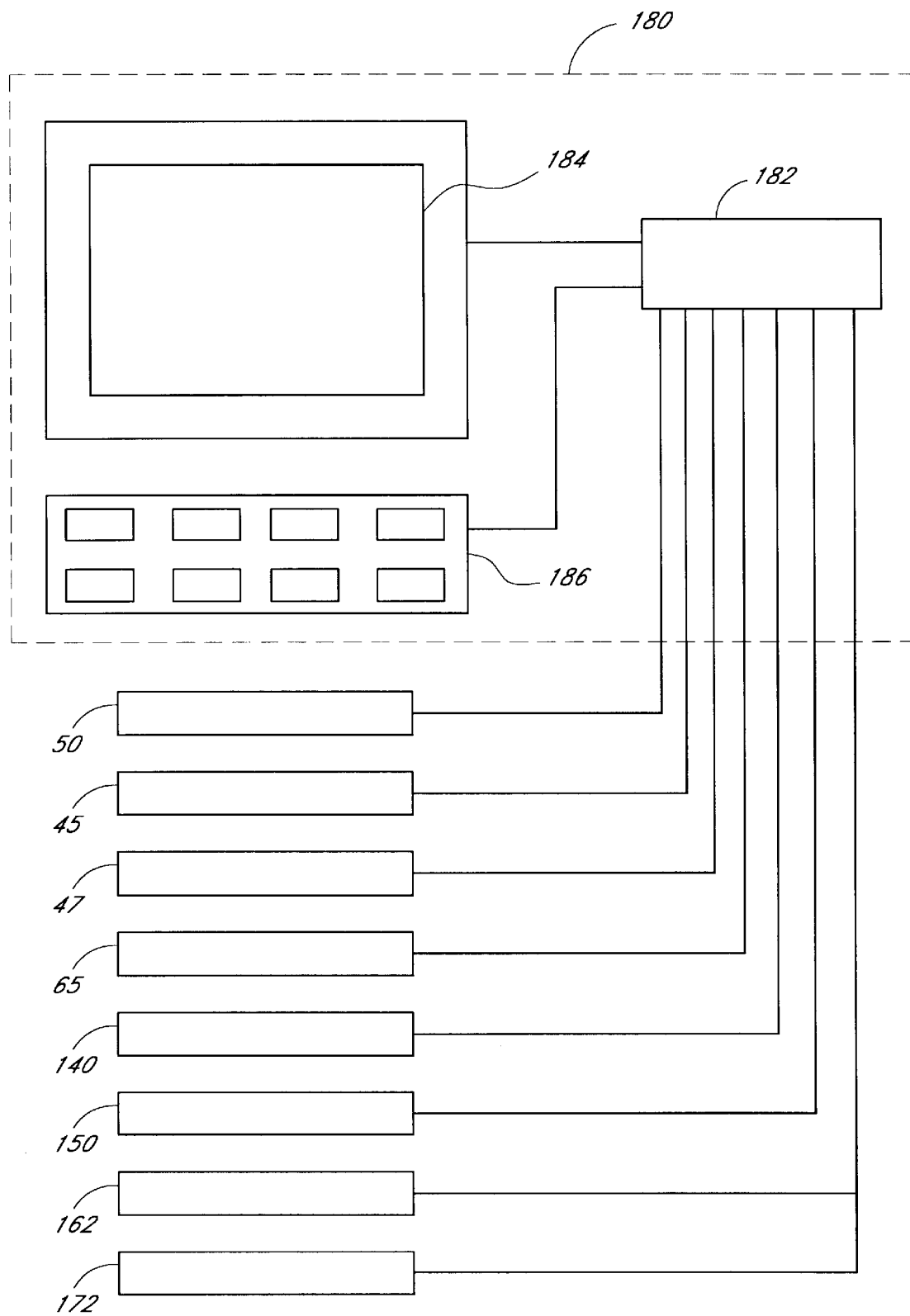
FIG. 10 schematically illustrates a system controller in accordance with an embodiment of the present invention.

In certain embodiments, as schematically illustrated in FIG. 10, various components of the sterilization system 10 are coupled to a system controller 180 which comprises a microprocessor 182, a display 184, and a user interface 186. The microprocessor 182 of such a system controller 180 is coupled to various components of the sterilization system 10, including, but not limited to, the electron gun 50, the cover interlock 45, the gas valve 47, the spindle actuators 65, the tube actuator 140, the peristaltic pump 150, the clamp actuator 162, and the system cover interlock 172. The microprocessor 182 is responsive to user input from the user interface 186 and to status signals from various components of the sterilization system 10 to generate control signals to certain components of the sterilization system 10 and to provide the user with status information via the display 184. Persons skilled in the art are able to provide a system controller 180 compatible with embodiments of the present invention.

Figure 11:
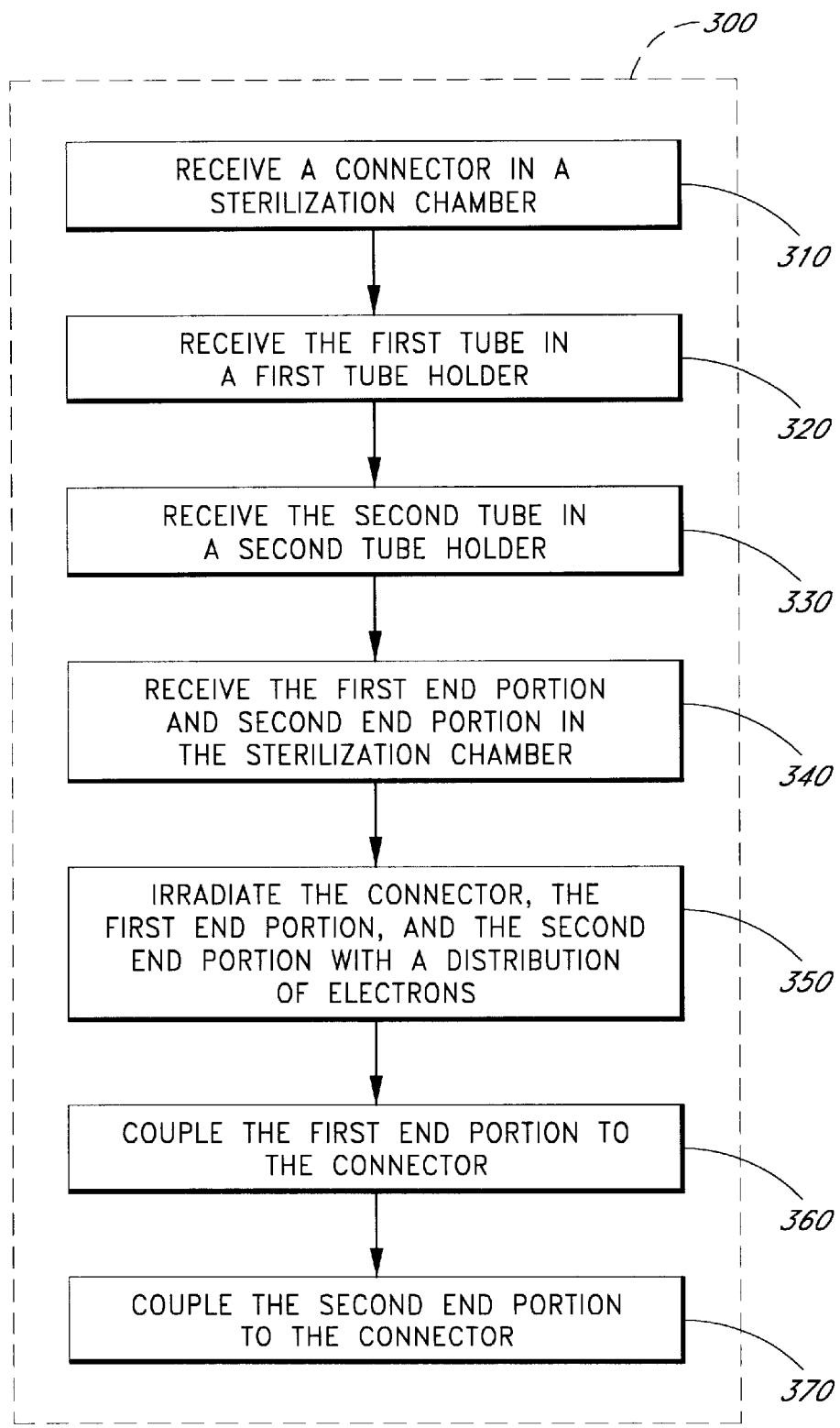
FIG. 11 is a flow diagram of a method for sealing together under sterile conditions the first end portion of the first tube and the second end portion of the second tube in accordance with an embodiment of the present invention.

FIG. 11 is a flow diagram of a method 300 in accordance with an embodiment of the present invention. The method 300 seals together under sterile conditions the first end portion 20 of the first tube 22 and the second end portion 30 of the second tube 32. The flow diagrams presented herein are described with reference to various elements described herein and in other figures. Persons skilled in the art are able to recognize that, while the flow diagrams presented herein illustrate particular embodiments with steps in a particular order, other embodiments with different orders of steps are also compatible with the present invention.

In an operational block 310, the connector 90 is received in the sterilization chamber 40. In certain embodiments, the connector 90 is placed in the holder 70, which is rotatable about the spindle 60. As is described more fully below, the holder 70 and the connector 90 are designed to fit together to facilitate moving the connector 90 in relation to the distribution of electrons in the sterilization chamber 40 and coupling the connector 90 to the first end portion 20 and second end portion 30.

In an operational block 320, the first tube 22 is received in the first tube holder 100. The first tube holder 100 has curved walls 120 which are movably coupled to the sterilization chamber 40. Similarly, in an operational block 330, the second tube 32 is received in the second tube holder 110. The second tube holder 110 has curved walls 130 which are movably coupled to the sterilization chamber 40. In embodiments in which the first tube holder 100 comprises a first top portion 104 and a first bottom portion 106, as schematically illustrated in FIG. 6, the first tube 22 is placed in the first tube holder 100 by first separating and then reconnecting the first top portion 104 and first bottom portion 106. Similarly in certain embodiments, the second tube 32 is placed in the second tube holder 110 by first separating and then reconnecting the second top portion 114 and the second bottom portion 116 of the second tube holder 110.

In an operational block 340, the first end portion 20 and the second end portion 30 are received in the sterilization chamber 40. In certain embodiments, the first end portion 20 is placed in the sterilization chamber 40 as the first tube 22 is placed in the first tube holder 100 by placing the first tube 22 so that the first end portion 20 extends from the first tube holder 100 into the sterilization chamber 40. Similarly in certain embodiments, the second end portion 30 is placed in the sterilization chamber 40 as the second tube 32 is placed in the second tube holder 110 by placing the second tube 32 so that the second end portion 30 extends from the second tube holder 110 into the sterilization chamber 40.

Figure 12:
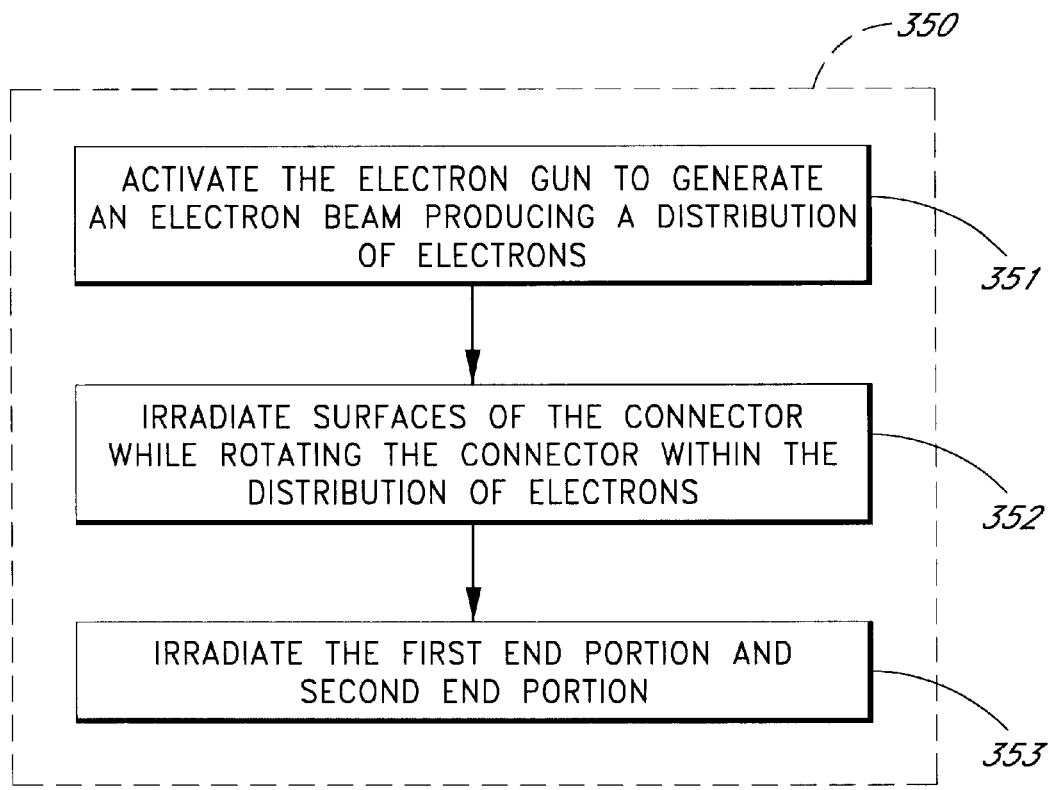
FIG. 12 is a flow diagram of an operational block corresponding to irradiating the connector, the first end portion, and the second end portion with the distribution of electrons in accordance with an embodiment of the present invention.

In an operational block 350, the connector 90, the first end portion 20 and the second end portion 30 are irradiated with the distribution of electrons. FIG. 12 is a flow diagram of the operational block 350 of one embodiment in accordance with the present invention. In an operational block 351, the electron gun 50 is activated to generate the electron beam which is directed through the electron hole 49 into the sterilization chamber 40 where it interacts both elastically and inelastically with the chamber walls 41 and other components within the sterilization chamber 40 to produce the distribution of electrons.

Biological spores to be irradiated in embodiments of the present invention typically have sizes of approximately 6–9 microns, and in certain circumstances, the spores may be positioned on top of one another. Therefore, in such embodiments, the distribution of electrons advantageously comprises electrons which can penetrate a distance of approximately 12–18 microns. Typically, electrons with kinetic energies of at least approximately 40 keV can penetrate these distances. In addition, the energies of x rays produced by the distribution of electrons increases with increasing electron kinetic energy, thereby requiring additional shielding. The distribution of electrons of embodiments of the present invention comprises electrons with kinetic energies preferably between approximately 40 keV and approximately 125 keV, more preferably between approximately 40 keV and approximately 100 keV, and most preferably between approximately 55 keV and 75 keV.

When electrons with sufficient kinetic energies impinge metal surfaces, such as the metallic inside surfaces 42 of the chamber walls 41 of the sterilization chamber 40, x rays are generated. These x rays propagate in straight lines and can propagate through various materials, such as plastics and polymers. The x rays can also propagate through metal walls, but in certain embodiments, proper material selection can limit or eliminate the x ray propagation. Examples of materials which are compatible with embodiments of the present invention include, but are not limited to, steel or hard anodized aluminum. Upon impinging a metal surface, a fraction of the incident x rays is reflected from the metal surface and a fraction of the incident x rays is absorbed by the metal surface. To prevent the propagation of the x rays out of the sterilization system 10, certain embodiments of the present invention comprise first and second tube holders 100, 110 with curved walls 120, 130 which have a general "S"-type shape. The curved walls 120, 130 are shaped so that an x ray can not propagate out of the sterilization system 10 without interacting at least three times with the metal surfaces of the sterilization chamber 40 or the first and second tube holders 100, 110. In this way, the x rays generated by the distribution of electrons in the sterilization chamber 40 are prevented from propagating outside the sterilization system 10 and the fraction of the x rays which propagate outside the sterilization system 10 is kept to acceptable levels. In certain embodiments, theses acceptable levels are defined by government regulations, such as 21 C.F.R. §1020.40 which provides radiological health standards for cabinet x ray systems. Other shapes can be used advantageously to cause the x rays to be reflected at least three times.

In an operational block 352, surfaces of the connector 90 are irradiated while rotating the connector 90 within the distribution of electrons. As is described more fully below, the irradiated surfaces are in fluid contact with the interior of the first tube 22 and the interior of the second tube 32 upon coupling the first end portion 20 to the connector 90 and coupling the second end portion 30 to the connector 90. In certain embodiments, the connector 90 is positioned within the distribution of electrons so that the surfaces of the connector 90 are impinged by electrons of the electron beam before the electrons interact with other components within the sterilization chamber 40. Rotating the connector 90 in such embodiments thereby facilitates irradiating all surfaces of the connector 90 which will be in fluid contact with the interior of the tubes 22, 32.

In an operational block 353, the first end portion 20 and the second end portion 30 are irradiated by the distribution of electrons. In certain embodiments, the first end portion 20 and the second end portion 30 are moved within the distribution of electrons while being irradiated to vary the amount and direction of the irradiation. While irradiation of the first end portion 20 and the second end portion 30 are included together in the operational block 353, persons skilled in the art recognize that the irradiation of the first and second end portions 20, 30 in certain embodiments can occur separately.

In certain embodiments, irradiating 350 the connector 90, the first end portion 20, and the second end portion 30 is performed while the sterilization chamber 40 is filled with a gas. In certain such embodiments, the gas is flowed into the sterilization chamber 40 after the gas is irradiated by the distribution of electrons. For example, as schematically illustrated in FIG. 3, the gas hole 47 is in fluid communication with the sterilization chamber 40 via the electron hole 49. The sterilization chamber 40 is filled with gas flowing from the gas source 46 through the gas hole 47 and through the electron hole 49. In embodiments in which the electron gun 50 is activated while gas is flowed into the sterilization chamber 40, the gas is irradiated by the electron beam while the gas is in the region between the gas hole 47 and the electron hole 49. For gases comprising multi-atomic molecules, such as diatomic molecules, irradiation of the gas in certain embodiments can excite the molecules into excited states (such excited molecules are sometimes called excimers). In certain embodiments, these excimers can contribute to the efficacy of the sterilization process.

Figure 13:
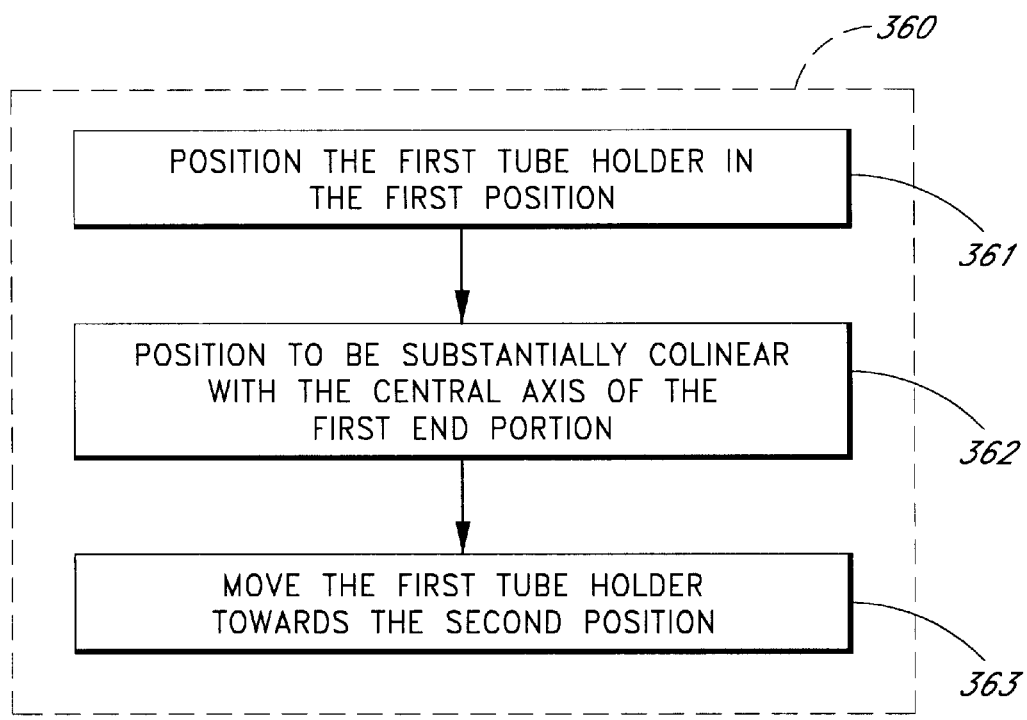
FIG. 13 is a flow diagram of an operational block corresponding to coupling the first end portion of the first tube to the connector in accordance with an embodiment of the present invention.

In the operational block 360, the first end portion 20 of the first tube 22 is coupled to the connector 90. FIG. 13 is a flow diagram of the operational block 360 of one embodiment in accordance with the present invention in which the connector 90 comprises a generally cylindrical first bore having a first axis as described below. In an operational block 361, the first tube holder 100 is positioned in the first position (i.e., such that the first end portion 20 is spaced away from the connector 90). In an operational block 362, the connector 90 is positioned to be substantially colinear with the central axis of the first end portion 20. In an operational block 363, the first tube holder 100 is moved towards the second position, thereby fitting the first end portion 20 onto the generally cylindrical first bore of the connector 90. In this way, the first end portion 20 is coupled to the connector 90.

Similarly, in the operational block 370, the second end portion 30 of the second tube 32 is coupled to the connector 90. In embodiments in which the connector 90 comprises a generally cylindrical second bore having a second axis as described below, the second tube holder 110 is moved towards the second position, thereby fitting the second end portion 39 onto the generally cylindrical second bore of the connector 90. In this way, the second end portion 30 is coupled to the connector 90, and fluid coupling is provided between the first and second tubes 22, 32 and transport of microorganisms is prevented between an interior of the tubes 22,32 and an exterior of the tubes 22, 32. In certain embodiments, coupling the second end portion 30 to the connector 90 occurs substantially concurrently with coupling the first end portion 20 to the connector 90. In certain embodiments, the first and second tubes 22, 32 coupled by the connector 90 are then removed from the sterilization chamber 40 and the first and second tube holders 100, 110.

Figure 14:
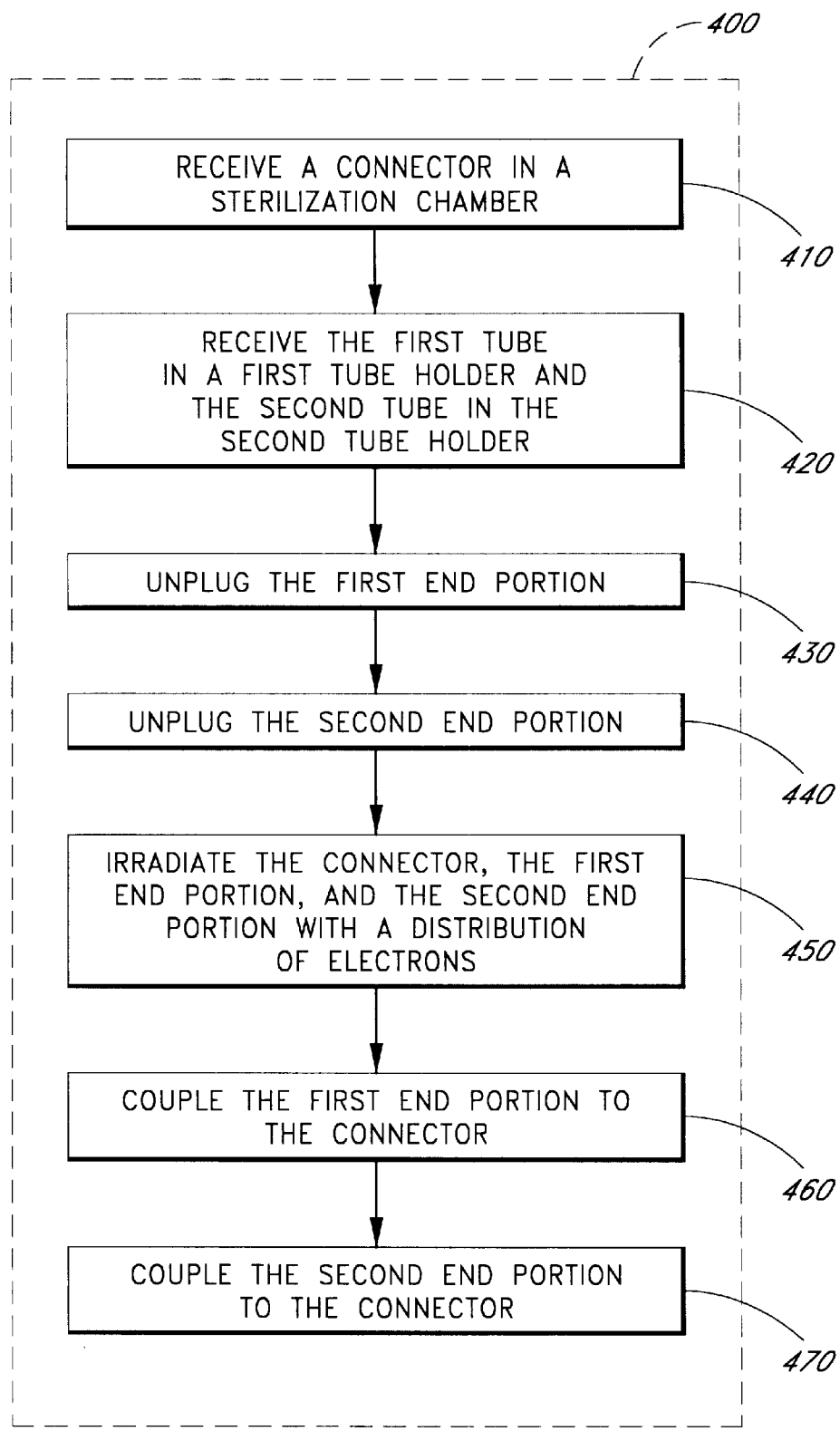
FIG. 14 is a flow diagram of a method for sealing together under sterile conditions a first end portion of the first tube initially sealed by a first plug and a second end portion of the second tube initially sealed by a second plug in accordance with another embodiment of the present invention.

FIG. 14 is a flow diagram of a method 400 in accordance with another embodiment of the present invention. The method 400 seals together under sterile conditions the first end portion 20 of the first tube 22 and the second end portion 30 of the second tube 32. The first end portion 20 is initially plugged by a first plug 200 and the second end portion 30 is initially plugged by a second plug 210. In this way, transport of microorganisms across the respective end portions 20, 30 is prevented. In certain embodiments, the plugs 200, 210 comprise a barrier film which is sealed across the respective end portions 20, 30. The plugs 200, 210 of other embodiments comprise constrictions of the first tube 22 and second tube 32 which effectively seal closed the respective end portions 20, 30. In certain other embodiments, as is described more fully below, the plugs 200, 210 each comprise a plug body with a generally cylindrical stopper portion which fits into and seals the respective end portions 20, 30 of the first tube 22 and second tube 32.

In an operational block 410, the connector 90 is received in the sterilization chamber 40. In certain embodiments, the connector 90 is placed in the holder 70 which is rotatable about the spindle 60. As is described more fully below, the holder 70 and the connector 90 are designed to fit together to facilitate moving the connector 90 in relation to the distribution of electrons in the sterilization chamber 40 and coupling the connector 90 to the first end portion 20 and second end portion 30.

In an operational block 420, the first tube 22 is received in the first tube holder 100 and the second tube 32 is received in the second tube holder 110. In embodiments in which the first tube holder 100 comprises the first top portion 104 and the first bottom portion 106, the first tube 22 is placed in the first tube holder 100 by separating then replacing the first top portion 104 and the first bottom portion 106. Similarly in certain embodiments, the second tube 32 is placed in the second tube holder 110 by separating then replacing the second top portion 114 and the second bottom portion 116.

Figure 15:
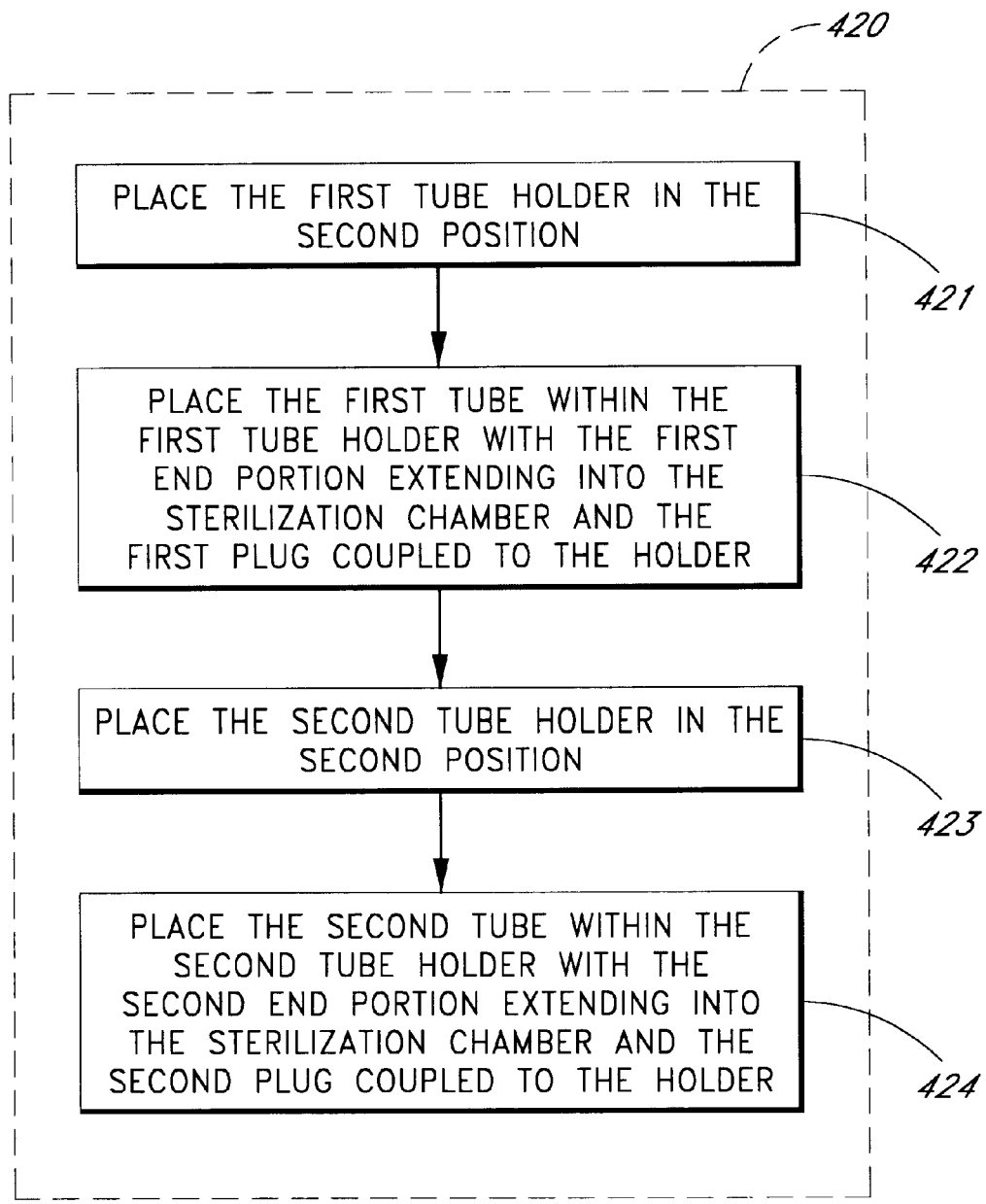
FIG. 15 is a flow diagram of an operational block corresponding to receiving the first tube in the first tube holder and the second tube in the second tube holder in accordance with an embodiment of the present invention.

FIG. 15 is a flow diagram of the operational block 420 of one embodiment in accordance with the present invention in which the plugs 200, 210 each comprise a generally cylindrical stopper portion as described below. In an operational block 421, the first tube holder 100 is placed in the second position. In an operational block 422, the first tube 22 is placed within the first tube holder 100 with the first end portion 20 extending into the sterilization chamber 40 and the first plug 200 is coupled to the holder 70. In an operational block 423, the second tube holder 110 is placed in the second position. In an operational block 424, the second tube 32 is placed within the second tube holder 110 with the second end portion 30 extending into the sterilization chamber 40, and the second plug 210 is coupled to the holder 70.

In an operational block 430, the first end portion 20 is unplugged by removing the first plug 200 from the first end portion 20. In embodiments in which the first plug 200 is coupled to the holder 70, unplugging the first end portion 20 comprises moving the first end portion 20 away from the holder 70 by moving the first tube holder 100 from the second position to the first position.

In an operational block 440, the second end portion 30 is unplugged by removing the second plug 210 from the second end portion 30. In embodiments in which the second plug 210 is coupled to the holder 70, unplugging the second end portion 30 comprises moving the second end portion 30 away from the holder 70 by moving the second tube holder 110 from the second position to the first position. In certain embodiments, unplugging 440 the second end portion 30 occurs substantially concurrently with unplugging 430 the first end portion 20.

In an operational block 450, the connector 90, the first end portion 20 and the second end portion 30 are irradiated with the distribution of electrons. In certain embodiments, irradiating the connector 90, the first end portion 20 and the second end portion 30 comprises the steps described above in relation to the operational block 350.

In certain embodiments, irradiating the connector 90, the first end portion 20 and the second end portion 30 in the block 450 further comprises monitoring the distribution of electrons and responding by modifying the distribution of electrons. In certain such embodiments, a current monitor which generates a signal in response to the electron beam current injected into the sterilization chamber 40 is coupled to the system controller 180. Examples of current monitors include, but are not limited to, an electrical circuit within the electron gun 50 or a sensor located within the sterilization chamber 40. In response to the signals generated by the current monitor, the system controller 180 can transmit control signals to the electron gun 50 to adjust the electron beam current to maintain a predetermined level. Persons skilled in the art are able to provide a current monitor and to monitor the distribution of electrons in accordance with embodiments of the present invention.

In an operational block 460, the first end portion 20 is coupled to the connector 90, and in an operational block 470, the second end portion 30 is coupled to the connector 90. In certain embodiments, coupling the first and second end portions 20, 30 to the connector 90 comprises steps similar to the steps described above in relation to the operational blocks 360, 370.

In certain embodiments in which the first end portion 20 of the first tube 22 is initially plugged by the first plug 200, an interior pressure inside the first tube 22 is reduced to be less than an external pressure outside the first end portion 20. For example, the first tube 22 can be coupled to the peristaltic pump 150. By activating the peristaltic pump 150 before the first plug 200 is removed from the first end portion 20, the interior pressure inside the first tube 22 can be reduced to be below the exterior pressure outside the first end portion 20. In this way, removal of the first plug 200 results in an inward rush of gas from outside the first end portion 20 to inside the first tube 22, thereby reducing the probability of microorganisms escaping from inside the first tube 22 into the sterilization chamber 40.

Figure 16:
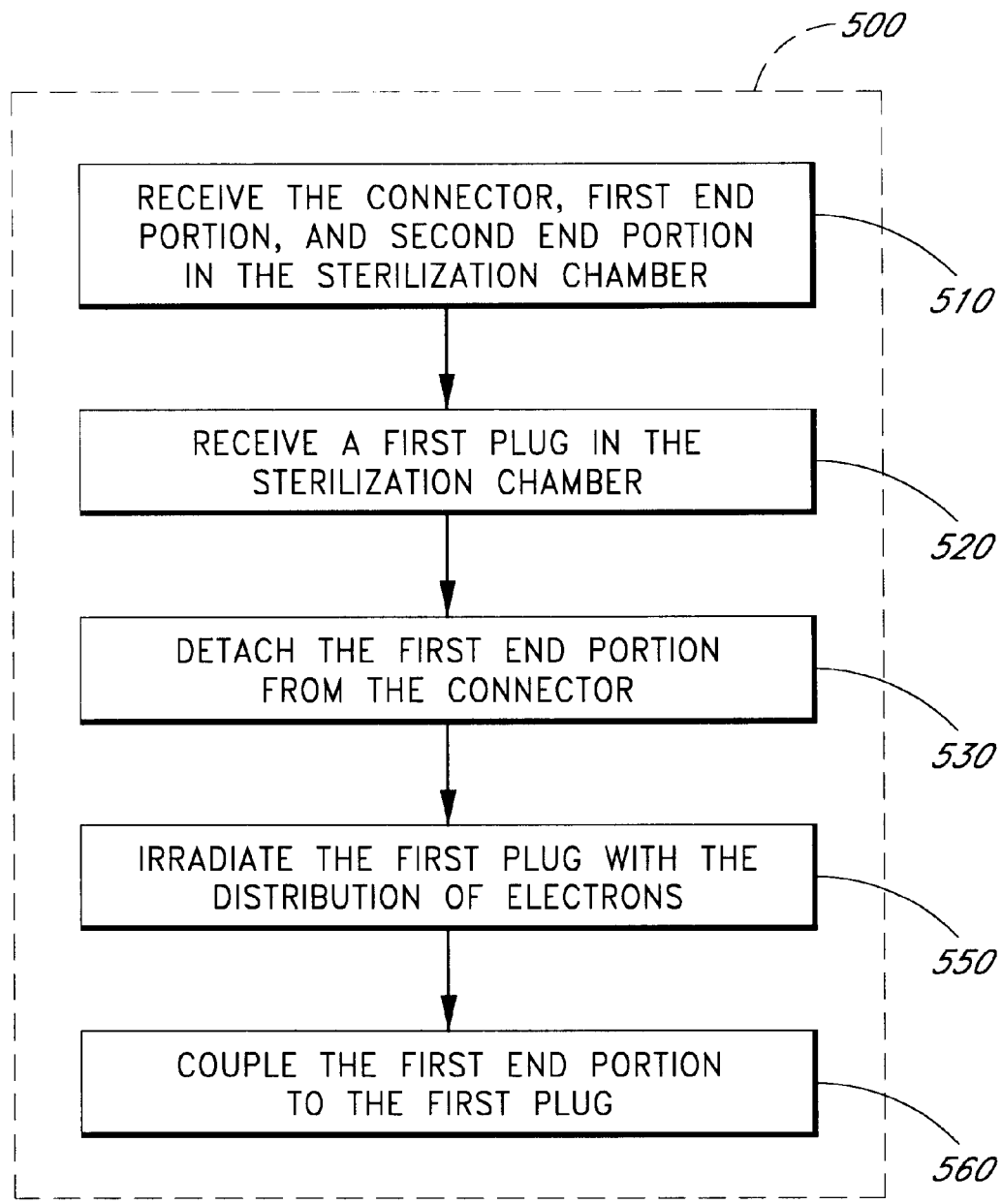
FIG. 16 is a flow diagram of a method for sealing closed under sterile conditions the first end portion of the first tube in accordance with another embodiment of the present invention.

FIG. 16 is a flow diagram of a method 500 in accordance with another embodiment of the present invention. The method 500 operates under sterile conditions to seal closed the first end portion 20 of the first tube 22. The first end portion 20 is initially sealed together via the connector 90 with the second end portion 30 of the second tube 22 to provide fluid coupling between the first and second tubes 22, 32.

In an operational block 510, the connector 90, the first end portion 20 and the second end portion 30 are received in the sterilization chamber 40. In certain embodiments, the first and second tube holders 100, 110 are placed in the second position and the first and second end portions 20, 30 are placed within the respective tube holders 100, 110. In addition, the connector 90 is placed in the holder 70.

In an operational block 520, a first plug 200 is received in the sterilization chamber 40. In certain embodiments in which the connector 90 and the first plug 200 are both designed to be coupled to the holder 70 concurrently, the first plug 200 is placed in the holder 70 along with the connector 90.

In an operational block 530, the first end portion 20 is detached from the connector 90. In certain embodiments, detaching the first end portion 20 in the block 530 comprises moving the first tube holder 100 towards the first position, thereby moving the first end portion 20 of the first tube 22 away from the connector 90. In certain embodiments, the second end portion 30 is also detached from the connector 90 by moving the second tube holder 110 towards the first position, thereby moving the second end portion 30 of the second tube 32 away from the connector 90. In certain embodiments, detaching the second end portion 30 occurs substantially concurrently with detaching the first end portion 20 in the block 530.

In an operational block 550, the first plug 200 is irradiated with the distribution of electrons. In certain embodiments, irradiating the first plug 200 comprises the steps similar to those described above in relation to irradiating the connector 90, the first end portion 20 and the second end portion 30 in the operational block 350. In particular, in certain embodiments, the holder 70 is positioned and rotated within the distribution of electrons to irradiate the surfaces of the first plug 200 which are in fluid contact with the interior of the first tube 22 upon coupling the first end portion 20 with the first plug 200.

In an operational block 560, the first end portion 20 is coupled to the first plug 200. In embodiments in which the first plug 200 comprises a generally cylindrical stopper portion, the first tube holder 100 is positioned in the first position and the first plug 200 is positioned to be substantially colinear with the central axis of the first end portion 20. The first tube holder 100 is then moved towards the second position, thereby fitting the first end portion 20 onto the generally cylindrical stopper portion. In this way, the first end portion 20 is coupled to the first plug 200 and transport of microorganisms between the interior of the first tube 22 and an exterior of the first tube 22 is prevented.

In certain embodiments, the method 500 further comprises receiving a second plug 210 in the sterilization chamber 40. In certain such embodiments in which the connector 90, the first plug 200 and the second plug 210 are designed to be coupled to the holder 70 concurrently, the second plug 210 is placed in the holder 70 along with the connector 90 and the first plug 200. The method 500 of other embodiments further comprises irradiating the second plug 210 with the distribution of electrons, detaching the second end portion 30 from the connector 90, and coupling the second end portion 30 to the second plug 210. In this way, transport of microorganisms between an interior of the second tube 32 and an exterior of the second tube 32 is prevented.

Figure 17:
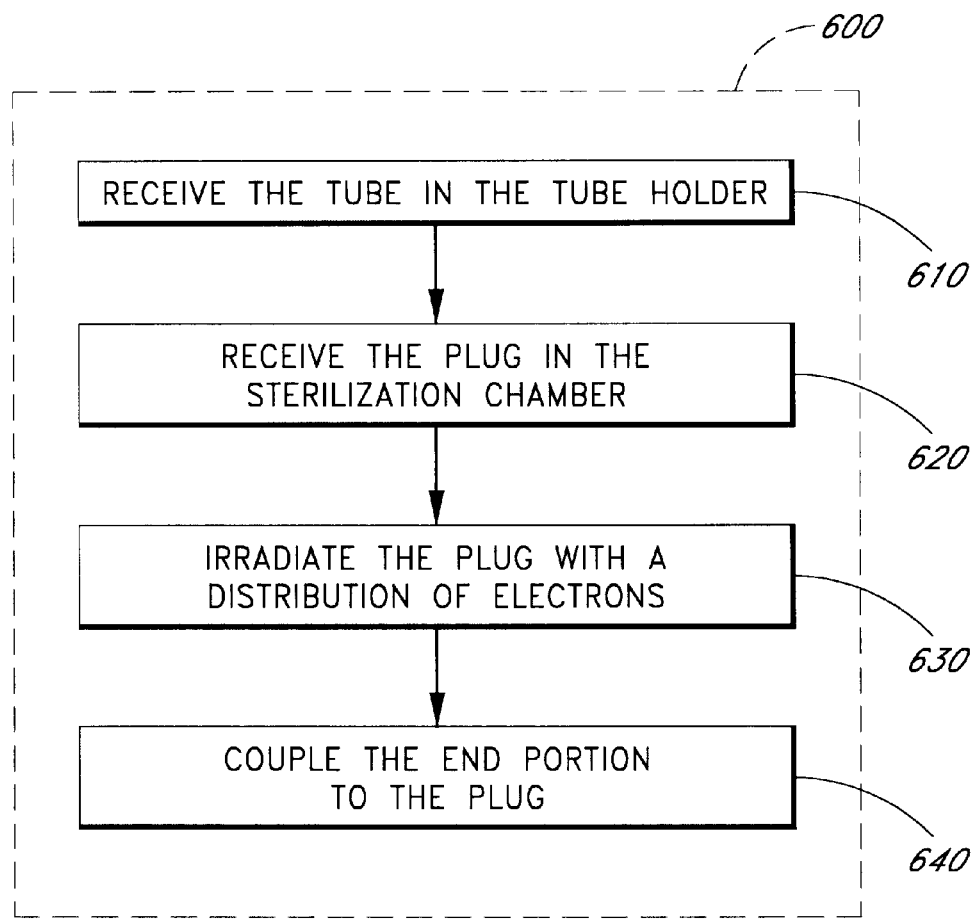
FIG. 17 is a flow diagram of a method for sealing closed under sterile conditions an end portion of a tube in accordance with another embodiment of the present invention.

FIG. 17 is a flow diagram of a method 600 in accordance with another embodiment of the present invention. The method 600 seals closed under sterile conditions an end portion 20 of a tube 22. In an operational block 610, the tube 22 is received in a tube holder 100 having curved walls 120 movably coupled to a sterilization chamber 40. The end portion 20 extends into the sterilization chamber 40. In certain embodiments, the tube holder 100 is placed in the second position and the tube 22 is placed within the tube holder 100.

In an operational block 620, a plug 200 is received in the sterilization chamber. In certain embodiments, the plug 200 is placed in the holder 70. In an operational block 630, the plug 200 is irradiated with a distribution of electrons. In certain embodiments, irradiating the plug 200 comprises the steps similar to those described above in relation to irradiating the connector 90, the first end portion 20 and the second end portion 30 in the operational block 350. In particular, in certain embodiments, the holder 70 is positioned and rotated within the distribution of electrons to irradiate the surfaces of the plug 200 which are in fluid contact with the interior of the tube 22 upon coupling the end portion 20 with the plug 200.

In an operational block 640, the end portion 20 is coupled to the plug 200. In embodiments in which the plug 200 comprises a generally cylindrical stopper portion, the curved walls 120 of the tube holder 100 are positioned in the first position and the plug 200 is positioned to be substantially colinear with the central axis of the end portion 20. The curved walls 120 of the tube holder 100 are then moved towards the second position, thereby fitting the end portion 20 onto the generally cylindrical stopper portion. In this way, the end portion 20 is coupled to the plug 200, and transport of microorganisms between the interior of the tube 22 and an exterior of the first 22 is prevented.

Figure 18:
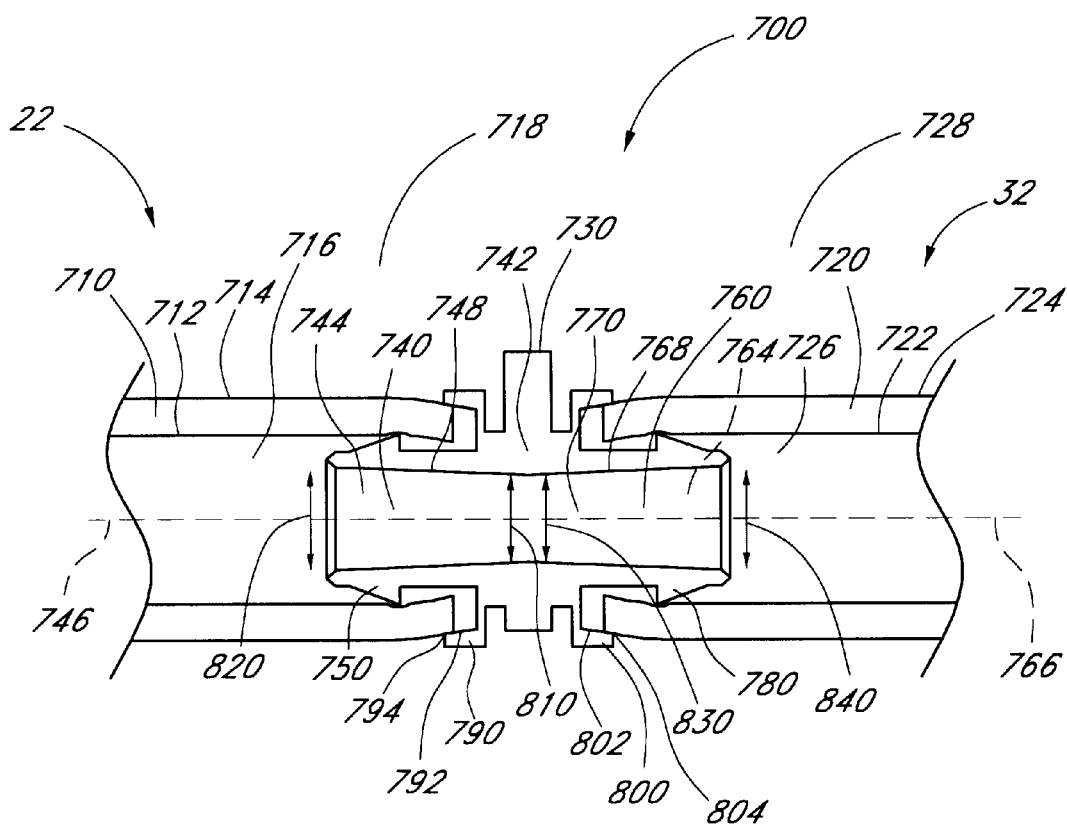
FIG. 18 schematically illustrates a connector for coupling a first tube to a second tube in accordance with an embodiment of the present invention.

FIG. 18 schematically illustrates a connector 700 for coupling a first tube 22 to a second tube 32 in accordance with embodiments of the present invention. The first tube 22 has a first tube wall 710 with a first inner surface 712 and a first outer surface 714, with the first tube wall 710 defining a first interior region 716 and a first exterior region 718. Similarly, the second tube 32 has a second tube wall 720 with a second inner surface 722 and a second outer surface 724, with the second tube wall 720 defining a second interior region 726 and a second exterior region 728.

The connector 700 comprises a body 730 and a generally cylindrical first bore 740 extending from a center portion 742 of the body 730 to a first distal portion 744 of the body 730. The first bore 740 also has a first axis 746 and a flared first inner bore surface 748. The connector 700 further comprises a first annular barb fitting 750 around the first distal portion 744 of the body 730.

The connector 700 further comprises a generally cylindrical second bore 760 extending from the center portion 742 of the body 730 to a second distal portion 764 of the body 730. The second bore 760 also has a second axis 766 and a flared second inner bore surface 768. The first bore 740 and the second bore 760 define a conduit 770 through which fluid can flow. The connector 700 further comprises a second annular barb fitting 780 around the second distal portion 764 of the body 730.

The connector 700 further comprises a first retaining collar 790 around the body 730. The first retaining collar 790 has a flared first inner collar surface 792. The first retaining collar 790 provides a first positive connection 794 with the first tube 22, whereby the first positive connection 794 prevents transport of microorganisms between the first interior region 716 and the first exterior region 718 of the first tube 22. The connector 700 further comprises a second retaining collar 800 around the body 730. The second retaining collar 800 has a flared second inner collar surface 802. The second retaining collar 800 provides a second positive connection 804 with the second tube 32, whereby the second positive connection 804 prevents transport of microorganisms between the second interior region 726 and the second exterior region 728 of the second tube 32.

In certain embodiments, the connector 700 is produced as a single piece and comprises the same material throughout. For example, the connector 700 of certain embodiments comprises a plastic or polymer material which is extruded into a mold. Upon solidification, the form is removed, thereby freeing the connector 700. Examples of other materials compatible with embodiments of the present invention include, but are not limited to, acrylonitrile-butadiene-styrene (ABS), acetal, polyamide, polycarbonate, thermoplastic polyester, polyethylene, polyphenylene sulfide, polyproplyene, polystyrene, polytetrafluoroethylene such as Teflon® available from E. I. du Pont Nemours and Company of Wilmington, Del., 300 series steel, styrene-acrylonitrile, and vinyl. Persons skilled in the art are able to provide methods of fabrication of the connector 700 in accordance with embodiments of the present invention.

In certain embodiments, as schematically illustrated in FIG. 18, the flared first inner bore surface 748 has an inner diameter 810 at the center portion 742 that is smaller than an inner diameter 820 at the first distal portion 744 of the body 730. The flared second inner bore surface 768 has an inner diameter 830 at the center portion 742 that is smaller than an inner diameter 840 at the second distal portion 764 of the body 730. The shapes of the first inner bore surface 748 and the second inner bore surface 768 are advantageous for at least two reasons. First, when plastic extrusion methods are used to fabricate the connector 700, the flared inner bore surfaces 748, 768 facilitate removal of the connector 700 from portions of the mold which define these surfaces 748, 768 since the distal portions of these bore surfaces 748, 768 are wider than the center portions. Second, in embodiments in which the connector 700 is rotated within the distribution of electrons during the irradiation of the connector 700, the flared shapes of the inner bore surfaces 748, 768 facilitate complete direct exposure of these surfaces 748, 768 by the electron beam. In this way, the inner bore surfaces 748, 768 are irradiated by more electrons with the maximum kinetic energy available in the distribution of electrons, which may increase the efficacy of the sterilization process with regard to these surfaces 748, 768. Similarly, in certain embodiments, the first inner collar surface 792 and the second inner collar surface 802 of the connector 700 are flared outward so that these surfaces 792, 802 can be directly exposed to the electron beam.

Figure 19A:
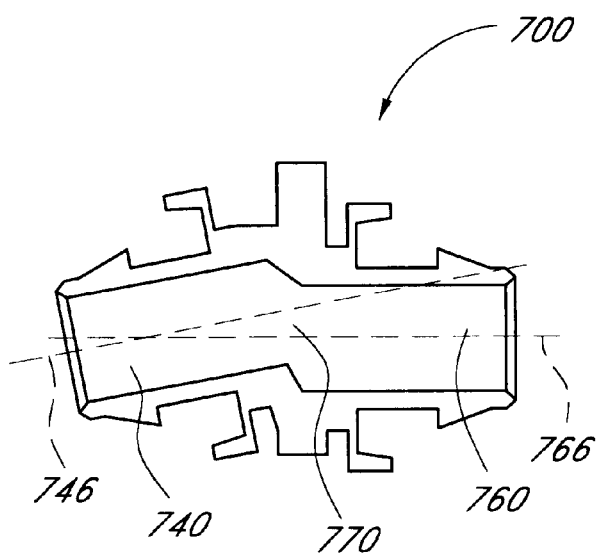
FIG. 19A schematically illustrates a connector in which the first and second axes are not colinear and define an angle in accordance with an embodiment of the present invention.
Figure 19B:
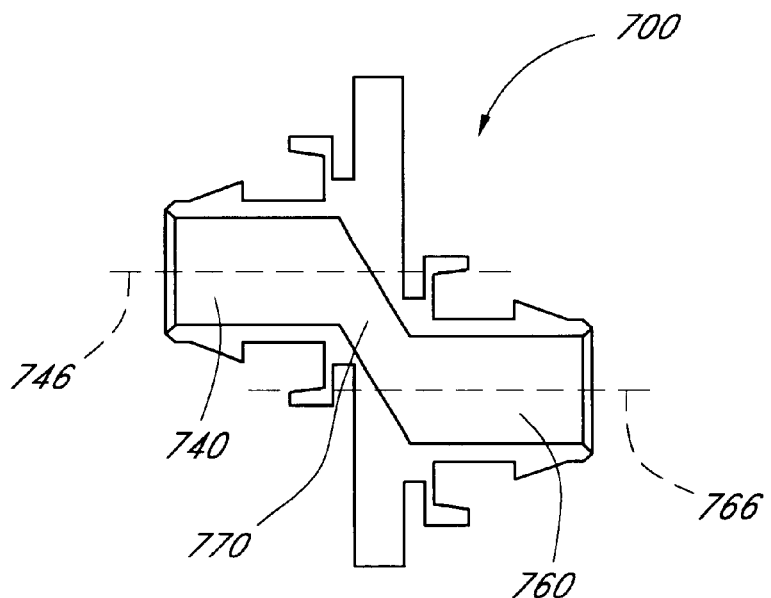
FIG. 19B schematically illustrates a connector in which the first and second axes are not colinear and do not intersect in accordance with an embodiment of the present invention.

In certain embodiments, the first axis 746 and the second axis 766 are colinear, as schematically illustrated in FIG. 18. In other embodiments, as schematically illustrated in FIG. 19A, the first axis 746 and the second axis 766 are not colinear, but intersect to define an angle. In still other embodiments, as schematically illustrated in FIG. 19B, the first axis 746 and second axis 766 are not colinear and do not intersect. However, in each of these embodiments, the first bore 740 and the second bore 760 define a conduit 770 through which fluid can flow.

In certain embodiments, the center portion 742 of the body 730 is adapted to be held by a holder 70. As schematically illustrated in FIG. 18, in embodiments in which the connector 700 is to be coupled to the holder 70 schematically illustrated in FIGS. 2, 4, and 5, the shape of the center portion 742 of the body 730 fits into the slotted fork portion 71 of the holder 70. Other configurations of the holder 70 and the center portion 742 of the body 730 are compatible with embodiments of the present invention.

Figure 20:
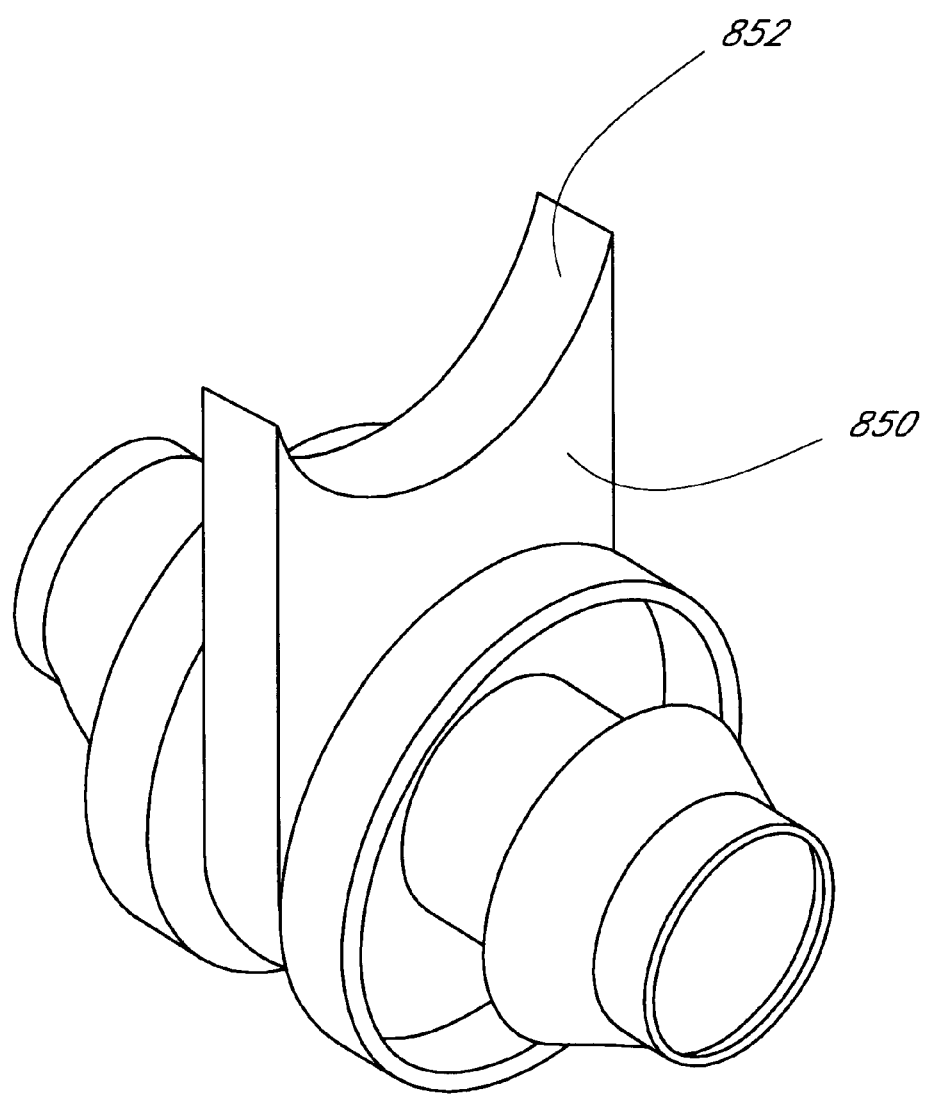
FIG. 20 schematically illustrates a connector comprising a tab with an arcuate surface in accordance with an embodiment of the present invention.
Figure 21:
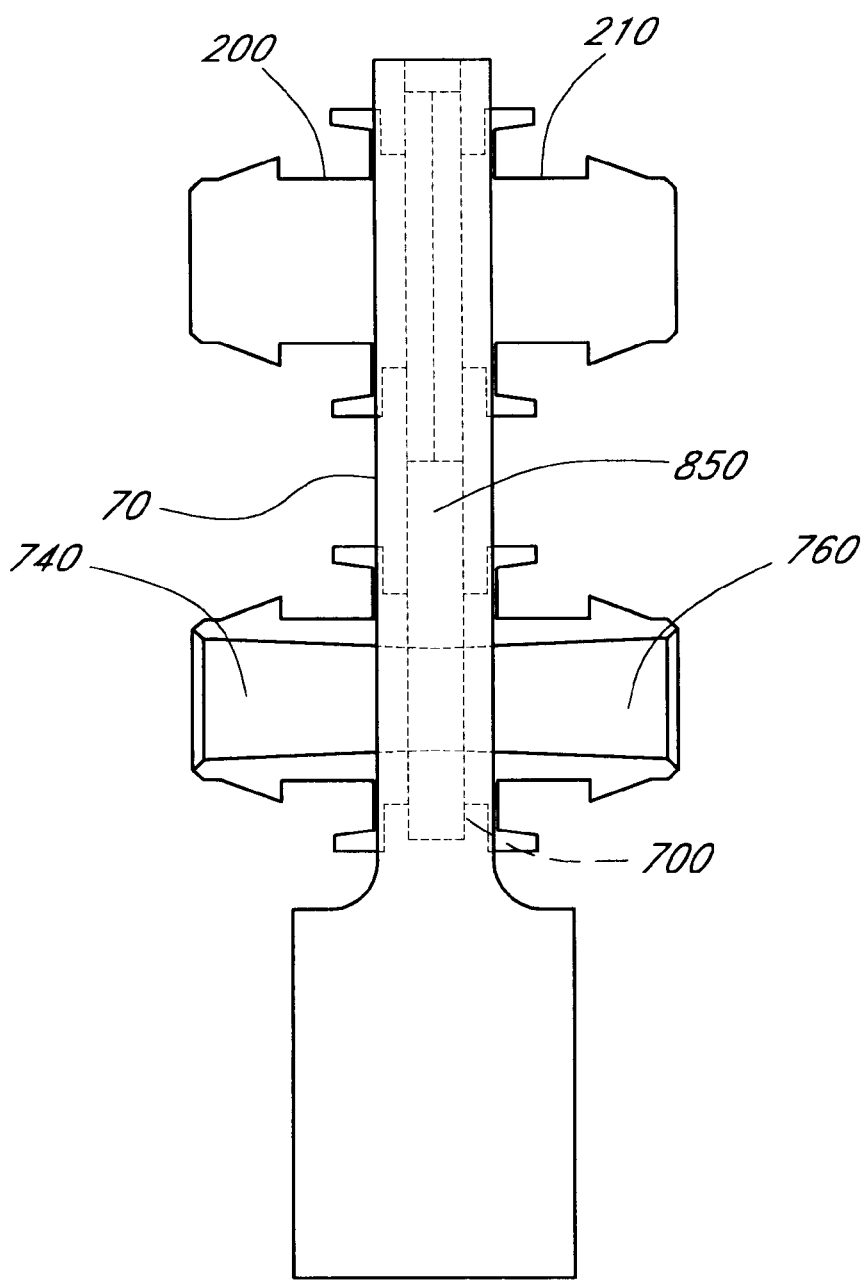
FIG. 21 schematically illustrates a pair of plugs supported by the tab in conjunction with the holder in accordance with an embodiment of the present invention.

In certain embodiments, as schematically illustrated in FIG. 20, the center portion 742 of the body 730 comprises a tab 850 which has an arcuate surface 852 adapted to support a plug 200 held by the holder 70. The tab 850 of certain embodiments in conjunction with the holder 70 supports the plug 200 so that the stopper portion of the plug 200 is substantially parallel with the first bore 740 of the connector 700. In still other embodiments, as schematically illustrated in FIG. 21, a pair of plugs 200, 210 are supported by the tab 850 in conjunction with the holder 70 so that the stopper portions of the plugs 200, 210 are substantially parallel with the first and second bores 740, 760 of the connector 700. Using such a configuration, the holder 70 can be linearly translated to align either the connector 700 or the plugs 200, 210 with the first and second end portions 20, 30 of the first and second tubes 22, 32.

When the first tube 22 is coupled to the connector 700, as schematically illustrated in FIG. 18, the first annular barb fitting 750 fits in the first interior region 716 of the first tube 22, and the first retaining collar 790 fits around the first outer surface 714 of the first tube 22. In certain such embodiments, the first annular barb fitting 750 presses against the first inner surface 712 of the first tube 22 and is dimensioned so as to push the first tube wall 710 outward. The first inner collar surface 792 contacts the first outer surface 714 of the first tube 22, and this contact is more forceful in embodiments in which the first tube wall 710 is pushed outward by the first annular barb fitting 750. The contact between the first outer surface 714 of the first tube 22 and the first inner collar surface 792 of the connector 700 provides the first positive connection 794 between the connector 700 and the first tube 22. Besides strengthening the first positive connection 794, the interaction of the first annular barb fitting 750 of the connector 700 with the first inner surface 712 of the first tube 22 provides a source of friction to maintain the coupling of the connector 700 with the first tube 22.

In certain embodiments, the second annular barb fitting 780 interacts with the second inner surface 722 of the second tube 32 in a similar manner to push the second tube wall 720 outward. In this way, the contact between the second inner collar surface 802 of the connector 700 and the second outer surface 724 of the second tube 32 is strengthened and provides the second positive connection 804 between the connector 700 and the second tube 32. The interaction of the second annular barb fitting 780 with the second inner surface 722 of the second tube 32 also provides friction which maintains the coupling of the connector 700 with the second tube 32.

Figure 22:
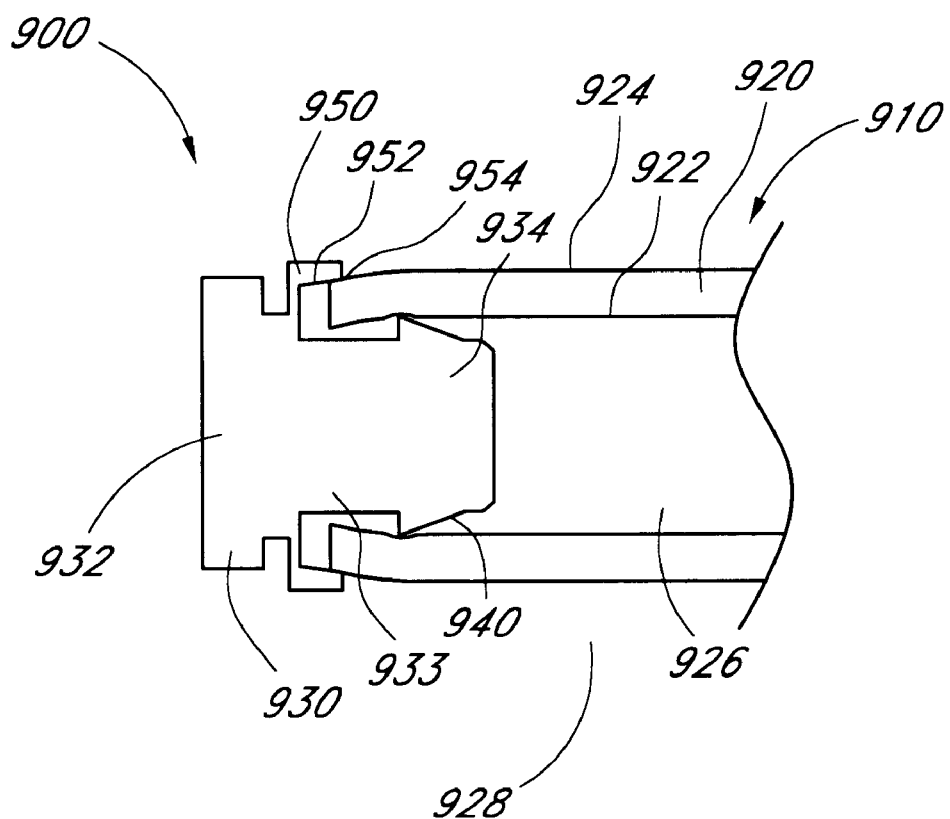
FIG. 22 schematically illustrates a plug in accordance with an embodiment of the present invention.

FIG. 22 schematically illustrates a plug 900 for sealing a tube 910 having a tube wall 920 with an inner surface 922 and an outer surface 924 in accordance with embodiments of the present invention. The tube wall 920 defines an interior region 926 and an exterior region 928. The plug 900 comprises a plug body 930 and a center portion 932 of the plug body 930 adapted to be held by a holder 70 and supported by the arcuate surface 852 of a connector 700. The connector 700 of certain embodiments comprises the connector body 730, the first bore 740, the first annular barb fitting 750, the second bore 760, the second annular barb fitting 780, the first retaining collar 790, and the second retaining collar 800 as described above.

The plug 900 further comprises a generally cylindrical stopper portion 933 extending from the center portion 932 of the plug body 930 to a distal portion 934 of the plug body 930. The plug 900 further comprises a third annular barb fitting 940 around the distal portion 934 of the plug body 930. The plug 900 further comprises a third retaining collar 950 around the plug body 930. The third retaining collar 950 has a flared inner collar surface 952. The third retaining collar 950 provides a positive connection 954 with the tube 910, and the positive connection 954 prevents transport of microorganisms between the interior region 926 and the exterior region 928.

In certain embodiments, the third annular barb fitting 940 interacts with the inner surface 922 of the tube 910 in a similar manner as described above in relation to the connector 700. The third annular barb fitting 940 pushes the tube wall 920 outward, thereby strengthening the contact between the inner collar surface 952 of the plug 900 and the outer surface 924 of the tube 910. Furthermore the third annular barb fitting 940 provides the positive connection 954 between the plug 900 and the tube 910. The interaction of the third annular barb fitting 940 with the inner surface 922 of the tube 910 also provides friction which maintains the coupling of the plug 900 with the tube 910.

As described above in relation to the connector 700, the plug 900 can be produced as a single piece and comprises the same material throughout. For example, the plug 900 of certain embodiments comprises a plastic or polymer material which is extruded into a mold. The flared inner collar surface 952 of the plug 900 can serve to facilitate removal of the plug 900 from portions of the mold which define this surface 952. Also, in embodiments in which the plug 900 is rotated within the distribution of electrons during the irradiation of the plug 900, the flared shape of the inner collar surface 952 facilitates complete direct exposure of this surface 952 by the electron beam.

Various embodiments of the present invention have been described above. Although this invention has been described with reference to these specific embodiments, the descriptions are intended to be illustrative of the invention and are not intended to be limiting. Various modifications and applications may occur to those skilled in the art without departing from the true spirit and scope of the invention as defined in the appended claims.

What is claimed is:

1. A sterilization system that seals a first end portion of a first tube and a second end portion of a second tube under sterile conditions, the sterilization system comprising:
   a sterilization chamber;
   an electron gun coupled to the sterilization chamber, the electron gun generating a distribution of electrons in the sterilization chamber, the electrons generating x rays upon impinging surfaces within the sterilization chamber;
   a spindle having at least a portion in the sterilization chamber, the spindle rotatably and linearly positionable with respect to the distribution of electrons;
   a holder coupled to the spindle, the holder releasably receiving a connector, whereby linearly positioning the spindle places the connector in the distribution of electrons and whereby rotating the spindle rotates the connector within the distribution of electrons; and
   first and second tube holders which receive the first and second tubes respectively, each tube holder having curved walls movably coupled to the sterilization chamber to move between a first position where the respective end portion is separated from the connector and a second position where the respective end portion is coupled to the connector, each curved wall having a shape such that the x rays generated within the sterilization chamber undergo at least three interactions with the curved walls before propagating outside the tube holders.

2. The sterilization system of claim 1, wherein the first and second end portions have a first state in which each end portion is independently sealed to prevent transport of microorganisms through the end portion, and a second state in which the end portions are sealed together via the connector to provide fluid coupling between the first and second tubes and to prevent transport of microorganisms between an interior of the tubes and an exterior of the tubes, whereby the sterilization system is adapted to transform the first and second end portions between the first state and the second state.

3. The sterilization system of claim 1, wherein the holder further releasably receives a first plug and a second plug, whereby linearly positioning the spindle places the first and second plugs in the distribution of electrons and whereby rotating the spindle rotates the first and second plugs within the distribution of electrons, the curved walls being further movably coupled to the sterilization chamber to move each end portion in the distribution of electrons between a third position coupled to the respective plug and a fourth position separated from the respective plug.

4. The sterilization system of claim 3, wherein the first end portion is initially sealed by the first plug and the second end portion is initially sealed by the second plug.

5. The sterilization system of claim 1, wherein the sterilization chamber comprises a stainless steel surface inside the sterilization chamber.

6. The sterilization system of claim 1, wherein the sterilization chamber comprises a hard coat anodized aluminum surface inside the sterilization chamber.

7. The sterilization system of claim 1, further comprising a gas in the sterilization chamber, the gas flowing into the sterilization chamber after being irradiated by the electrons from the electron gun.

8. The sterilization system of claim 7, wherein the gas comprises helium.

9. The sterilization system of claim 7, wherein the gas comprises nitrogen.

10. The sterilization system of claim 1, wherein the distribution of electrons comprises electrons with kinetic energies between approximately 40 keV and approximately 125 keV.

11. The sterilization system of claim 1, wherein the distribution of electrons comprises electrons with kinetic energies between approximately 40 keV and approximately 100 keV.

12. The sterilization system of claim 1, wherein the distribution of electrons comprises electrons with kinetic energies between approximately 55 keV and approximately 75 keV.

13. The sterilization system of claim 1, further comprising a control system coupled to the electron gun and to an electron current monitor, the control system responsive to feedback signals from the electron current monitor to adjust the distribution of electrons.

14. The sterilization system of claim 1, further comprising a peristaltic roller pump coupled to the first tube, whereby an internal pressure inside the first tube is less than an external pressure outside the first tube.

15. A method of sealing together under sterile conditions a first end portion of a first tube and a second end portion of a second tube, the method comprising:
   receiving a connector in a sterilization chamber;
   receiving the first tube in a first tube holder, the first tube holder having curved walls movably coupled to the sterilization chamber;
   receiving the second tube in a second tube holder, the second tube holder having curved walls movably coupled to the sterilization chamber;
   receiving the first end portion and the second end portion in the sterilization chamber;
   irradiating the connector, the first end portion, and the second end portion with a distribution of electrons;
   coupling the first end portion to the connector; and
   coupling the second end portion to the connector, thereby providing fluid coupling between the first and second tubes and preventing transport of microorganisms between an interior of the tubes and an exterior of the tubes.

16. A method of sealing together under sterile conditions a first end portion of a first tube and a second end portion of a second tube, the first end portion initially plugged by a first plug and the second end portion initially plugged by a second plug, thereby preventing transport of microorganisms across the respective end portion, the method comprising:
   receiving a connector in a sterilization chamber of a sterilization system;

receiving the first end portion and the second end portion in the sterilization chamber;

unplugging the first end portion by removing the first plug from the first end portion;

unplugging the second end portion by removing the second plug from the second end portion;

irradiating the connector, the first end portion, and the second end portion with a distribution of electrons;

coupling the first end portion to the connector; and coupling the second end portion to the connector, thereby providing fluid coupling between the first and second tubes and preventing transport of microorganisms between an interior of the tubes and an exterior of the tubes.

17. The method of claim 16, wherein unplugging the second end portion occurs substantially concurrently with unplugging the first end portion.

18. The method of claim 16, wherein:

receiving the first end portion and second end portion in the sterilization chamber comprises coupling the first plug to a holder and coupling the second plug to the holder;

removing the first plug comprises moving the first end portion away from the holder; and removing the second plug comprises moving the second end portion away from the holder.

19. The method of claim 16, wherein receiving the connector in the sterilization chamber comprises receiving the connector in a holder which is rotatable about a spindle.

20. The method of claim 19, wherein irradiating the connector with the distribution of electrons comprises irradiating surfaces of the connector while rotating the connector within the distribution of electrons, the surfaces being in fluid contact with the interior of the tubes upon coupling the first end portion to the connector and coupling the second end portion to the connector.

21. The method of claim 19, wherein coupling the first end portion to the connector comprises moving the first end portion towards the holder, and wherein coupling the second end portion to the connector comprises moving the second end portion towards the holder.

22. The method of claim 16, further comprising flowing gas into the sterilization chamber after the gas is irradiated by the distribution of electrons.

23. The method of claim 16, wherein the distribution of electrons comprises electrons with kinetic energies between approximately 40 keV and approximately 125 keV.

24. The method of claim 16, wherein the distribution of electrons comprises electrons with kinetic energies between approximately 40 keV and approximately 100 keV.

25. The method of claim 16, wherein the distribution of electrons comprises electrons with kinetic energies between approximately 55 keV and approximately 75 keV.

26. The method of claim 16, further comprising generating x rays by impinging surfaces in the sterilization chamber with the distribution of electrons and reducing a fraction of the x rays which propagate outside the sterilization system.

27. The method of claim 16, wherein irradiating the connector, the first end portion, and the second end portion further comprising monitoring the distribution of electrons and responding by modifying the distribution of electrons.

28. The method of claim 16, further comprising reducing an interior pressure inside the first tube to be less than an external pressure outside the first end portion.

29. A method of sealing closed under sterile conditions a first end portion of a first tube, the first end portion initially sealed together via a connector with a second end portion of a second tube to provide fluid coupling between the first and second tubes, the method comprising:

receiving the connector, the first end portion, and the second end portion in a sterilization chamber;

receiving a first plug in the sterilization chamber;

detaching the first end portion from the connector;

irradiating the first plug with a distribution of electrons; and coupling the first end portion to the first plug, thereby preventing transport of microorganisms between an interior of the first tube and an exterior of the first tube.

30. The method of claim 29, wherein receiving the connector comprises receiving the connector in a holder and detaching the first end portion from the connector comprises moving the first end portion away from the holder.

31. The method of claim 29, wherein receiving the first plug in the sterilization chamber comprises receiving the first plug in a holder which is rotatable about a spindle.

32. The method of claim 31, wherein irradiating the first plug with the distribution of electrons comprises irradiating surfaces of the first plug while rotating the first plug, the surfaces being in fluid contact with the interior of the first tube upon coupling the first end portion to the first plug.

33. The method of claim 31, wherein coupling the first end portion to the first plug comprises moving the first end portion towards the holder.

34. The method of claim 29, further comprising receiving a second plug in the sterilization chamber, irradiating the second plug with the distribution of electrons, detaching the second end portion from the connector, and coupling the second end portion to the second plug, thereby preventing transport of microorganisms between an interior of the second tube and an exterior of the second tube.

35. The method of claim 29, further comprising flowing gas into the sterilization chamber after the gas is irradiated by the distribution of electrons.

36. The method of claim 29, wherein the distribution of electrons comprises electrons with kinetic energies between approximately 40 keV and approximately 125 keV.

37. The method of claim 29, wherein the distribution of electrons comprises electrons with kinetic energies between approximately 40 keV and approximately 100 keV.

38. The method of claim 29, wherein the distribution of electrons comprises electrons with kinetic energies between approximately 55 keV and approximately 75 keV.

39. The method of claim 29, further comprising generating x rays by impinging surfaces in the sterilization chamber with the distribution of electrons and preventing the x rays from propagating outside the sterilization chamber.

40. The method of claim 29, further comprising monitoring the distribution of electrons and responding by modifying the distribution of electrons.

41. A method of sealing closed under sterile conditions an end portion of a tube, the method comprising:

receiving the tube in a tube holder having curved walls movably coupled to a sterilization chamber, the end portion extending into the sterilization chamber;

receiving a plug in the sterilization chamber;

irradiating the plug with a distribution of electrons; and coupling the end portion to the plug by moving the curved walls of the tube holder between a first position where the end portion is separated from the plug and a second position where the end portion is coupled to the plug, thereby preventing transport of microorganisms between an interior of the tube and an exterior of the tube.

42. A connector for coupling a first tube to a second tube, the first tube having a first tube wall with a first inner surface and a first outer surface, the first tube wall defining a first interior region and a first exterior region of the first tube, the second tube having a second tube wall with a second inner surface and a second outer surface, the second tube wall defining a second interior region and a second exterior region of the second tube, the connector comprising:

a body;

a generally cylindrical first bore extending from a center portion of the body to a first distal portion of the body and having a first axis and a flared first inner bore surface;

a first annular barb fitting around the first distal portion of the body;

a generally cylindrical second bore extending from the center portion of the body to a second distal portion of the body and having a second axis and a flared second inner bore surface, the first bore and second bore defining a conduit through which fluid can flow;

a second annular barb fitting around the second distal portion of the body;

a first retaining collar around the body, the first retaining collar having a flared first inner collar surface, the first retaining collar providing a first positive connection with the first tube, the first positive connection preventing transport of microorganisms between the first interior region and the first exterior region of the first tube; and a second retaining collar around the body, the second retaining collar having a flared second inner collar surface, the second retaining collar providing a second positive connection with the second tube, the second positive connection preventing transport of microorganisms between the second interior region and the second exterior region of the second tube.

43. The connector of claim 42, wherein the flared first inner bore surface has an inner diameter at the center portion that is smaller than an inner diameter at the first distal portion, and the second inner bore surface has an inner diameter at the center portion that is smaller than an inner diameter at the second distal portion.

44. The connector of claim 42, wherein the first axis and second axis are colinear.

45. The connector of claim 42, wherein the connector comprises extruded plastic.

46. The connector of claim 42, wherein the center portion of the body is adapted to be held by a holder.

47. The connector of claim 46, wherein the center portion of the body comprises a tab having an arcuate surface adapted to support a plug held by the holder.

48. A plug for sealing a tube having a tube wall with an inner surface and an outer surface, the tube wall defining an interior region and an exterior region of the tube, the plug comprising:

a plug body;

a center portion of the plug body adapted to be held by a holder and supported by the arcuate surface of a connector, the connector comprising:

a connector body;

a generally cylindrical first bore extending from a center portion of the connector body to a first distal portion of the connector body and having a first axis and a flared first inner bore surface;

a first annular barb fitting around the first distal portion of the connector body;

a generally cylindrical second bore extending from the center portion of the connector body to a second distal portion of the connector body and having a second axis and a flared second inner bore surface, the first bore and second bore defining a conduit through which fluid can flow;

a second annular barb fitting around the second distal portion of the connector body;

a first retaining collar around the connector body, the first retaining collar having a flared first inner collar surface; and a second retaining collar around the connector body, the second retaining collar having a flared second inner collar surface;

a generally cylindrical stopper portion extending from the center portion of the plug body to a distal portion of the plug body;

a third annular barb fitting around the distal portion of the plug body;

a third retaining collar around the plug body, the third retaining collar having a flared inner collar surface, the third retaining collar providing a positive connection with the tube, the positive connection preventing transport of microorganisms between the interior region and the exterior region of the tube.

* * * * *